(12) United States Patent
DeBusk et al.

(10) Patent No.: US 6,754,883 B2
(45) Date of Patent: Jun. 22, 2004

(54) MODULAR ANALYSIS AND STANDARDIZATION SYSTEM

(75) Inventors: Brian C. DeBusk, Clinton, TN (US); Elizabeth C. DeBusk, Clinton, TN (US); Mark W. Shanks, Clinton, TN (US); Michael C. Cofer, Knoxville, TN (US); W. Francis Lukens, Knoxville, TN (US)

(73) Assignee: GE Medical Systems Information Technologies, Inc., Milwaukee, WI (US)

(*) Notice: Subject to any disclaimer, the term of this patent is extended or adjusted under 35 U.S.C. 154(b) by 638 days.

(21) Appl. No.: 09/735,729

(22) Filed: Dec. 11, 2000

(65) Prior Publication Data

US 2002/0116300 A1 Aug. 22, 2002

Related U.S. Application Data

(63) Continuation-in-part of application No. 09/382,710, filed on Aug. 24, 1999, now Pat. No. 6,314,556.

(51) Int. Cl.$^7$ ................................................ G06F 9/45
(52) U.S. Cl. ......................... 717/107; 717/120; 705/2
(58) Field of Search ............................... 717/107, 120; 705/2; 700/29, 30, 32, 36, 28; 706/45

(56) References Cited

U.S. PATENT DOCUMENTS

| | | | |
|---|---|---|---|
| 4,174,598 A | 11/1979 | Shepherd et al. | ............. 53/431 |
| 4,987,538 A | 1/1991 | Johnson et al. | ................. 705/2 |

(List continued on next page.)

FOREIGN PATENT DOCUMENTS

| | | | |
|---|---|---|---|
| EP | 0 556 093 A1 | 2/1993 | ........... B65B/61/20 |

OTHER PUBLICATIONS

Sethi, Ravi Programming Languages. New York: Addison Wesley. 1989, pp. 169–173 and 178–185.
Biggerstaff et al. Software Reusability. New York: Addison Wesley. 1989, vol. 2, pp. 269–287.

Primary Examiner—John Chavis
(74) Attorney, Agent, or Firm—Fletcher Yoder

(57) ABSTRACT

An information management system produces a standard bill of resources based on bills of resources that include a list of resources to be utilized in performing a procedure. The system includes a general purpose computer system with storage means, processing means, display means, and input means. Information management software installed on the general purpose computer includes node software objects providing a health care information management function, including a clinical pathway node software object, a case management node software object, and a standardization review node software object. The clinical pathway node software object creates clinical pathway module software objects, including resource software objects and container software objects. The standardization review node software object selects bills of resources from a known universe of bills of resources, and develops models corresponding to the selected bills of resources, where the models include values which correspond to a number of units of given resources from the selected bills of resources. The standardization review node software object mathematically manipulates the models to highlight similarities and dissimilarities of defined characteristics in the models, expresses the manipulated models in a format in which a relative position of each of the manipulated models may be determined, where the relative position of each of the manipulated models reflects the degree of similarity or dissimilarity to the other manipulated models, analyzes the selected bills of resources based upon the expression of the manipulated models, and produces the standard bill of resources based on the analysis of the selected bills of resources.

18 Claims, 9 Drawing Sheets

U.S. PATENT DOCUMENTS

| | | | | |
|---|---|---|---|---|
| 5,001,630 A | | 3/1991 | Wiltfong | 705/3 |
| 5,191,522 A | * | 3/1993 | Bosco et al. | 705/4 |
| 5,235,795 A | | 8/1993 | DeBusk | 53/467 |
| 5,287,267 A | | 2/1994 | Jayaraman et al. | 705/10 |
| 5,301,320 A | | 4/1994 | McAtee et al. | 705/9 |
| 5,319,543 A | | 6/1994 | Wilhelm | 705/3 |
| 5,325,293 A | | 6/1994 | Dorne | 705/2 |
| 5,517,405 A | | 5/1996 | McAndrew et al. | 706/45 |
| 5,557,514 A | | 9/1996 | Seare et al. | 705/2 |
| 5,583,758 A | | 12/1996 | McIlroy et al. | 705/2 |
| 5,594,638 A | | 1/1997 | Iliff | 705/3 |
| 5,596,502 A | | 1/1997 | Koski et al. | 700/95 |
| 5,682,728 A | * | 11/1997 | DeBusk et al. | 53/445 |
| 5,721,913 A | | 2/1998 | Ackroff et al. | 707/103 |
| 5,724,575 A | | 3/1998 | Hoover et al. | 707/10 |
| 5,732,401 A | | 3/1998 | Conway | 705/29 |
| 5,748,907 A | | 5/1998 | Crane | 705/2 |
| 5,826,239 A | | 10/1998 | Du et al. | 705/8 |
| 5,842,173 A | * | 11/1998 | Strum et al. | 705/1 |
| 5,845,254 A | | 12/1998 | Lockwood et al. | 705/2 |
| 5,991,728 A | * | 11/1999 | DeBusk et al. | 705/2 |
| 5,995,937 A | * | 11/1999 | DeBusk et al. | 705/2 |
| 6,113,540 A | * | 9/2000 | Iliff | 600/300 |
| 6,234,964 B1 | * | 5/2001 | Iliff | 600/300 |
| 6,283,761 B1 | * | 9/2001 | Joao | 434/236 |
| 6,314,556 B1 | * | 11/2001 | DeBusk et al. | 717/107 |
| 6,363,393 B1 | * | 3/2002 | Ribitzky | 707/102 |
| 6,381,576 B1 | * | 4/2002 | Gilbert | 705/2 |
| 6,581,204 B2 | * | 6/2003 | DeBusk et al. | 717/120 |
| 2002/0052539 A1 | * | 5/2002 | Haller et al. | 600/300 |

* cited by examiner

| Component | Description | Qty | Cost |
|---|---|---|---|
| 142 | FESS/SEPTO TRACEPAK | 1.00 | 82.36 |
| 91-DELV00010070 | DELV CARE EVENT | 1.00 | 17.81 |
| 92-DER00709 | DER SUPPLY BUNDLE FOR DELV | 1.00 | 17.81 |
| 56-11099 | BOX, TRACECART 20.5 X 19 X 34.375" | 1.00 | 1.65 |
| 56-11359R | BASE, RETRACE TRACECRT, 40 GAL | 1.00 | 10.00 |
| 56-52346 | LID, RETRACE, TRACECART | 1.00 | 6.00 |
| 56-52629 | LBL:"TRACEPAK IN PROCESS" 2 X 3 | 1.00 | 0.02 |
| 56-52630 | LBL:"TRACEPAK COMPLETE" 4 X 3 BLU | 1.00 | 0.04 |
| TPAK-LAB | LBL:8" BLNK WTE RL "TRCPK CONTE" | 1.00 | 0.10 |
| 91-OPER00010070 | OPER CARE EVENT | 1.00 | 64.55 |
| 92-DER00705 | DER SUPPLY BUNDLE FOR OPER | 1.00 | 47.65 |
| 25-002 | PAD, INSTR MAGNETIC 20 X 16 | 1.00 | 9.29 |
| 50-6066 | TRAY, NASAL | 0.33 | 88.71 |
| 50-6066P | NASAL TRAY | 1.00 | 29.57 |
| 5-0402 | NDL CTR, FOAM BLOCK/MAGNET 10CT | 1.00 | 0.64 |
| 5-1163 | GZE, 4 X 4 12 PLY NOXR INDEX 10 S | 9.99 | 0.20 |
| 5-1175 | GZE, 4 X 4 16 PLY XR BANDED 10 S | 9.99 | 0.50 |
| 5-1583 | BAG, STERILIZATION 27 X 34" 4MIL | 1.00 | 0.90 |
| 5-15926 | GWN, LG FAB-REIN CHST&SLV, ULTRA | 2.00 | 5.56 |
| 5-16988 | SPG, NEURO .5X3 PATT 10CR X R | 1.00 | 2.50 |
| 5-17748 | CVR, BK TBL 54 X 85 | 1.00 | 0.99 |
| 5-1871 | BOWL, 32 OZ SPONGE BLUE 1000CC | 1.00 | 0.12 |
| 5-1873 | BOWL, 16 OZ 500CC | 1.00 | 0.09 |
| 5-1887 | DISH, PETRI 100X 15MM W/O RING | 1.00 | 0.12 |
| 5-1892 | CUP, MEDICINE 2OZ (HKA0059990) | 1.00 | 0.04 |
| 5-2894 | NDL, 27 GX1-1/2"LL, RB, OR/ER, ST | 2.00 | 0.12 |
| 5-2919 | SYR, 20CC, LS (ST 520640) | 1.00 | 0.22 |
| 5-3033 | SYR, 5CC, LL (ST#309603) | 2.00 | 0.16 |
| 5-3049 | SYR, 3CC LL (513934) | 2.00 | 0.08 |
| 5-3107 | BAG, SUT 6.5 X 11.3 WT NON-LATEX | 2.00 | 0.06 |
| 5-3183 | BLD, 15, SS, ST | 2.00 | 0.44 |
| 5-3244 | TBG, SUCT 1/4 X 12 NC FEMALE/CONN | 2.00 | 1.36 |
| 5-4138 | CVR, MAYO STD 23 X 54, BL | 1.00 | 0.39 |
| 5-5042 | TWL, OR BLUE COTTON/NS | 9.99 | 7.50 |
| 5-5453 | CTA, 6" WOOD | 19.98 | 0.00 |
| 5-6111 | CUP, 4OZ SPECIMEN W/SCREW LID | 2.00 | 0.16 |
| 5-6240 | DRP, EENT SPLIT 72 X 115, W/TAPE | 1.00 | 4.61 |
| 5-6445 | TAPE STRIP, 2 X 5" W/DEROYAL LOGO | 1.00 | 0.04 |
| 5-9042 | DRP, BAR 44 X 38, W/TAPE | 1.00 | 1.28 |
| SA50-6066P-1 | TRAY W/SLEEVE PROTECTOR | 1.00 | 1.47 |
| 5-13188 | PROTECTOR, TRAY LARGE 18 X 26" | 1.00 | 0.79 |
| 5-1828 | TRAY, FLAT PLATFORM 15 X 13.5 X 1" | 1.00 | 0.68 |
| TRLAB-001 | LBL: DEROYAL 1-UP TRAY STER | 1.00 | 0.02 |
| 55-51260 | FOG INHIBITOR, ENDOMATE | 1.00 | 2.85 |
| 55-51947 | SPG, NEURO .5 X 3 PATT 10PK | 1.00 | 4.17 |
| M10-049 | PAD, WHEELCHAIR 20" X 6.5" X 3/4" | 3.00 | 1.80 |
| 92-OMI00705 | OMI SUPPLY BUNDLE FOR OPER | 1.00 | 16.90 |
| 001346200202 | EXTENSION SET 20 INCH STERILE | 1.00 | 0.56 |
| 001361380313 | SODIUM CHL 0.9% IRRIGATION | 1.00 | 0.00 |
| 0013V302401 | LINER 2000ML W/LID V30240101 | 2.00 | 2.74 |
| 1825003435 | TB CONN SUCT 1/4 | 2.00 | 2.30 |
| 3583001050 | DRSG TELFA STRL | 1.00 | 0.14 |
| 3642089601 | CVR STAND MAYO 23-1/2 | 1.00 | 2.00 |
| 4056004711 | BAGS LINEN O R | 1.00 | 0.38 |
| 4056004741 | BAG HEAVY DUTY RED 23 X 8 X 41 | 1.00 | 3.06 |
| 5817220100 | NDL PNL 22GX | 1.00 | 1.82 |
| 66080E0509 | VALLEY LAB CAUTERY BIPOLAR | 1.00 | 3.90 |

Fig. 4

| Component | Description | Usage | Each | Qty | Cost | 142 | 143 | 145 | 146 |
|---|---|---|---|---|---|---|---|---|---|
| 001346200202 | EXTENSION SET 20 INCH STERILE | 0.50 | 0.56 | 2.00 | 1.12 | 1.00 | | | 1.00 |
| 001361380313 | SODIUM CHL 0.9% IRRIGATION | 0.75 | 0.00 | 3.00 | 0.00 | 1.00 | 1.00 | | 1.00 |
| 001379730505 | WATER, STERILE FOR IRRIG | 0.25 | 2.05 | 1.00 | 2.05 | | | | 1.00 |
| 0013V302401 | LINER 2000ML W/LID v30240101 | 1.00 | 1.37 | 8.00 | 10.96 | 2.00 | 2.00 | 2.00 | 2.00 |
| 0421501007 | TB SUCT FLEX STRL | 0.25 | 0.97 | 1.00 | 0.97 | | 1.00 | | |
| 0723305128 | NDL SPEC USE 30GX1 | 0.25 | 0.79 | 1.00 | 0.79 | | 1.00 | | |
| 1825003435 | TB CONN SUCT 1/4 | 1.00 | 1.15 | 8.00 | 9.20 | 2.00 | 2.00 | 2.00 | 2.00 |
| 2478400426 | MERECO SLIM KENNEDY | 0.25 | 11.25 | 1.00 | 11.25 | | | | 1.00 |
| 25-002 | PAD, INSTR MAGNETIC 20 X 16 | 1.00 | 9.29 | 4.00 | 37.16 | 1.00 | 1.00 | 1.00 | 1.00 |
| 3583001050 | DRSG TELFA STRL | 0.50 | 0.14 | 2.00 | 0.28 | 1.00 | | | |
| 3642089601 | CVR STAND MAYO 23-1/2 | 1.00 | 2.00 | 4.00 | 8.00 | 1.00 | 1.00 | 1.00 | 1.00 |
| 4056004711 | BAGS LINEN O R | 1.00 | 0.38 | 4.00 | 1.52 | 1.00 | 1.00 | 1.00 | 1.00 |
| 4056004741 | BAG HEAVY DUTY RED 23 X 8 X 41 | 1.00 | 3.06 | 4.00 | 12.24 | 1.00 | 1.00 | 1.00 | 1.00 |
| 4509001179 | ELECTRODE ADH CONDU 2 SPLIT LG | 0.25 | 3.80 | 1.00 | 3.80 | | | 1.00 | |
| 5-0402 | NDL CTR, FOAM BLOCK/MAGNET 10CT | 1.00 | 0.64 | 4.00 | 2.56 | 1.00 | 1.00 | 1.00 | 1.00 |
| 5-1163 | GZE, 4 X 4 12 PLY NOXR INDEX 10S | 1.00 | 0.02 | 49.96 | 1.00 | 9.99 | 9.99 | 19.99 | 9.99 |
| 5-1175 | GZE, 4 X 4 16 PLY XR BANDED 10S | 1.00 | 0.05 | 39.96 | 2.00 | 9.99 | 9.99 | 9.99 | 9.99 |
| 5-1201 | SPG, TONSIL 1", SNGL STRNG NS | 0.25 | 0.07 | 5.00 | 0.35 | | | 5.00 | |
| 5-13188 | PROTECTOR, TRAY LARGE 18 X 26" | 1.00 | 0.79 | 5.00 | 3.95 | 1.00 | 1.00 | 2.00 | 1.00 |
| 5-1583 | BAG, STERILIZATION 27 X 34" 4MIL | 1.00 | 0.90 | 5.00 | 4.50 | 1.00 | 1.00 | 2.00 | 1.00 |
| 5-15926 | GWN, LG FAB-REIN CHST&SLV, ULTRA | 1.00 | 2.78 | 7.99 | 22.22 | 2.00 | 2.00 | 2.00 | 2.00 |
| 5-1595 | BAG, GLASSINE 3 X 5.5 (004) | 0.25 | 0.01 | 1.00 | 0.01 | | | 1.00 | |
| 5-1698 | SPG, NEURO .5 X 3 PATT 10CR X R | 1.00 | 2.50 | 4.00 | 9.99 | 1.00 | 1.00 | 1.00 | 1.00 |
| 5-17748 | CVR, BK TBL 54 X 85 | 1.00 | 0.99 | 5.00 | 4.95 | 1.00 | 1.00 | 2.00 | 1.00 |
| 5-1828 | TRAY, FLAT PLATFORM 15 X 13.5 X 1" | 1.00 | 0.68 | 5.00 | 3.40 | 1.00 | 1.00 | 2.00 | 1.00 |
| 5-1829 | TRAY, LG DEEP 9.72 X 5.4 X 2 | 0.25 | 0.15 | 1.00 | 0.15 | | | 1.00 | |
| 5-1871 | BOWL, 32 OZ SPONGE BLUE 1000CC | 1.00 | 0.12 | 5.00 | 0.60 | 1.00 | 1.00 | 2.00 | 1.00 |
| 5-1873 | BOWL, 16 OZ 500CC | 1.00 | 0.09 | 4.00 | 0.36 | 1.00 | 1.00 | 1.00 | 1.00 |
| 5-1887 | DISH, PETRI 100 X 15MM W/O RING | 1.00 | 0.12 | 4.00 | 0.48 | 1.00 | 1.00 | 1.00 | 1.00 |
| 5-1892 | CUP, MEDICINE 2 OZ (HKA0059990) | 1.00 | 0.04 | 6.00 | 0.24 | 1.00 | 1.00 | 3.00 | 1.00 |
| 5-2894 | NDL, 27GX1-1/2"LL, RB, OR/ER, ST | 1.00 | 0.06 | 7.99 | 0.48 | 2.00 | 2.00 | 2.00 | 2.00 |
| 5-2919 | SYR, 20CC, LS (ST 520640) | 1.00 | 0.22 | 4.00 | 0.88 | 1.00 | 1.00 | 1.00 | 1.00 |
| 5-3033 | SYR, 5CC, LL (ST#309603) | 1.00 | 0.08 | 7.99 | 0.64 | 2.00 | 2.00 | 2.00 | 2.00 |
| 5-3049 | SYR, 3CC LL (513934) | 1.00 | 0.04 | 7.99 | 0.32 | 2.00 | 2.00 | 2.00 | 2.00 |
| 5-3050 | SYR, IRRIG 50CC BULB | 0.25 | 0.28 | 1.00 | 0.28 | | | 1.00 | |
| 5-3056 | SYR, 12CC LL (512878) | 0.25 | 0.09 | 1.00 | 0.09 | | | 1.00 | |
| 5-3107 | BAG, SUT 6.5 X 11.3 WT NON-LATEX | 1.00 | 0.03 | 7.99 | 0.24 | 2.00 | 2.00 | 2.00 | 2.00 |
| 5-3183 | BLD, 15, SS, ST | 1.00 | 0.22 | 7.99 | 1.76 | 2.00 | 2.00 | 2.00 | 2.00 |
| 5-3244 | TBG, SUCT 1/4 X 12 NC FEMALE/CONN | 1.00 | 0.68 | 8.99 | 6.11 | 2.00 | 2.00 | 3.00 | 2.00 |
| 5-3274 | CATH, URETH ALL PURP RR 8FR 2E | 0.25 | 0.36 | 1.00 | 0.36 | | | 1.00 | |
| 5-3735 | SUCTCOAG, FOOTCTRL 6" 10FR | 0.25 | 7.38 | 1.00 | 7.38 | | | 1.00 | |
| 5-4138 | CVR, MAYO STD 23 X 54, BL | 1.00 | 0.39 | 5.00 | 1.95 | 1.00 | 1.00 | 2.00 | 1.00 |
| 5-5042 | TWL, OR BLUE COTTON /NS | 1.00 | 0.75 | 43.96 | 32.97 | 9.99 | 9.99 | 13.99 | 9.99 |
| 5-5453 | CTA, 6" WOOD | 1.00 | 0.00 | 79.92 | 0.00 | 19.98 | 19.98 | 19.98 | 19.98 |
| 5-6033 | BOX, 21.5 X 21.5 X 14" PRINTED | 0.25 | 1.58 | 0.20 | 0.32 | | | 0.20 | |
| 5-6111 | CUP, 4 OZ SPECIMEN W/SCREW LID | 1.00 | 0.08 | 7.99 | 0.64 | 2.00 | 2.00 | 2.00 | 2.00 |
| 5-6240 | DRP, EENT SPLIT 72 X 115, W/TAPE | 1.00 | 4.61 | 4.00 | 18.42 | 1.00 | 1.00 | 1.00 | 1.00 |
| 5-6445 | TAPE STRIP, 2 X 5" W/DERPYAL LOGO | 1.00 | 0.04 | 4.00 | 0.16 | 1.00 | 1.00 | 1.00 | 1.00 |
| 5-8284 | WRP, 48 X 48, KIMG REG | 0.25 | 0.27 | 1.00 | 0.27 | | | 1.00 | |
| 5-9042 | DRP, BAR 44 X 38, W/TAPE | 1.00 | 1.28 | 4.00 | 5.11 | 1.00 | 1.00 | 1.00 | 1.00 |
| 55-51260 | FOG INHIBITOR, ENDOMATE | 1.00 | 2.85 | 4.00 | 11.40 | 1.00 | 1.00 | 1.00 | 1.00 |
| 55-51947 | SPG, NEURO .5 X 3 PATT 10PK | 1.00 | 4.17 | 4.00 | 16.68 | 1.00 | 1.00 | 1.00 | 1.00 |
| 56-11099 | BOX, TRACECART 20.5 X 19 X 34.375" | 1.00 | 1.65 | 4.00 | 6.60 | 1.00 | 1.00 | 1.00 | 1.00 |
| 56-11359R | BASE, RETRACE TRACECRT, 40 GAL | 1.00 | 10.00 | 4.00 | 40.00 | 1.00 | 1.00 | 1.00 | 1.00 |
| 56-52346 | LID, RETRACE, TRACECART | 1.00 | 6.00 | 4.00 | 24.00 | 1.00 | 1.00 | 1.00 | 1.00 |
| 56-52629 | LBL:"TRACEPAK IN PROCESS" 2 X 3 | 1.00 | 0.02 | 4.00 | 0.08 | 1.00 | 1.00 | 1.00 | 1.00 |
| 56-52630 | LBL:"TRACEPAK COMPLETE" 4 X 3 BLU | 1.00 | 0.04 | 4.00 | 0.16 | 1.00 | 1.00 | 1.00 | 1.00 |
| 5817220100 | NDL SPNL 22GX | 0.75 | 1.82 | 3.00 | 5.46 | 1.00 | 1.00 | | 1.00 |
| 5937000370 | TONGUE BLADES JR. STERILE | 0.25 | 0.03 | 2.00 | 0.06 | | | 2.00 | |
| 66080E0509 | VALLEY LAB CAUTERY BIPOLAR | 1.00 | 3.90 | 4.00 | 15.60 | 1.00 | 1.00 | 1.00 | 1.00 |
| M10-049 | PAD, WHEELCHAIR 20" X 6.5" X 3/4" | 1.00 | 0.60 | 12.00 | 7.20 | 3.00 | 3.00 | 3.00 | 3.00 |
| TPAK-LAB | LBL: 8" BLNK WTE RL "TRCPK CONTE" | 1.00 | 0.10 | 4.00 | 0.40 | 1.00 | 1.00 | 1.00 | 1.00 |
| TRLAB-001 | LBL: DEROYAL 1-UP TRAY STER | 1.00 | 0.02 | 0.10 | 0.10 | 1.00 | 1.00 | 2.00 | 1.00 |

Fig.5

MODULAR ANALYSIS AND STANDARDIZATION SYSTEM

This application is a continuation in part of prior application Ser. No. 09/382,710 filed Aug. 24, 1999, now U.S. Pat. No. 6,314,556.

FIELD OF THE INVENTION

This invention relates to the field of analysis and development of bills of resources to be used during a procedure and, particularly, to a method for depicting relationships among different bills of resources and analyzing or refining resource utilization based thereon.

BACKGROUND OF THE INVENTION

Bills of resources are used in a variety of situations in order to insure that all of the resources necessary to perform certain tasks or procedures are available at the time that a procedure is to be performed. One of the simplest bills of resources would be a parts list for use during the assembly of an item. A more complex bill of resources might include a parts list as well as a list of required tools needed to complete the assembly of an item. For an extremely critical procedure, such as a medical operation, or the servicing of a vital component on an airplane or other piece of critical machinery, the bill of resources might well include parts, tools, equipment and labor resources required to perform the procedure.

In certain environments, similar procedures are conducted on a regular basis and, although the individuals performing the procedure may change or the procedure may vary slightly from one performance to the next, the necessary resources will be similar each time the procedure is performed. However, it is extremely likely that the resources allocated to the performance of the procedure from one time to the next will vary substantially based upon who is performing the procedure, variations in subjects of the procedure, when and where the procedure is performed, etc. Frequently, such variations in the bill of resources from each performance of the procedure will not reflect actual differing circumstances in the performance of the procedure, but will be a matter of habit, personal preference or even chance. However, it should be recognized that such variation adds costs and reduces efficiency. For example, such variation will likely require the stocking of multiple equivalent components in inventory which will tend to require the maintenance of a larger inventory and reduce discounts that might be received for bulk purchases of a single item. Furthermore, such variation reduces the accuracy of forecasts for required components, labor resources or equipment, since actual utilization will vary substantially from one performance to the next.

This problem is especially acute in the medical care field where substantial pressure is placed to reduce costs without compromising the quality of care. One trend is to move increasingly toward procedure-based unitized delivery systems in which a large portion of the supplies used in medical procedure are provided in one container. These systems allow for hospitals, and other health care facilities, to order just the supplies needed at the time a procedure is scheduled. Thus, the hospital may reduce their inventory of stocked supplies, labor associated with pulling supplies for a procedure, and use just-in-time ordering techniques which help to reduce costs. However, these procedure-based delivery systems have some drawbacks.

First, doctors are often very particular about the brand and style of medical supplies they use. For example, one doctor may prefer one brand of cautery pencil for his heart surgeries while a different doctor may prefer a different brand for the same surgery. Frequently, the number of doctor-preferred items will be large, thus requiring either that a number of different bills of resources be used for a given procedure, or that the hospital stock all of the doctor preference items and that they be pulled from inventory prior to performance of the procedure. However, these solutions often negate the advantages of the unitized delivery system since the stocking of doctor preference items will serve to increase inventory and labor requirements and the increase of bills of resources will prevent the supplier from generating economy of scale savings based on volume in a given bill of resources.

Also, these procedure-based unitized delivery systems do not address resource areas other than supplies. While supplies are a major component of a medical procedure, labor resources, reusable supplies and durable equipment are all important resources utilized in a medical procedure and their use should be analyzed and optimized.

Although the type and extent of possible benefits from bill of resource standardization have been desired for some time, the problem has been so complex that standardization has taken place on a superficial and ad hoc basis, when even attempted. For example, some healthcare facilities have opted into group purchasing plans in which the group will negotiate with certain suppliers for certain types of supplies in order to get the best price. With respect to this type of solution, for the few products affected, the best price may be obtained. However, such solutions typically relate only to small groups or classes of supplies and do not take into account actual usage history, real doctor preferences, procedure-specific requirements and certainly do not address labor, re-usable supplies, and durable equipment resource utilization. There is simply no consistent, logical and proven method for the standardization of procedure-based bills of resources.

The problem of bill of resource standardization and optimization is a complex one. For a relatively common procedure, such as a heart bypass operation, a vast number of different resources must be utilized. The list of medical supplies for the procedure runs many pages and a wide variety of labor and equipment resources must be brought together at just the right time. If the resources are expressed in mathematical terms, you get a problem with potentially hundreds of variables. Furthermore, each individual heart bypass procedure is a new mathematical problem with an equally large number of variables. Thus, simple and known analytical techniques are not readily adaptable to the problem of analyzing and optimizing bills of resources.

What is needed, therefore, is an integrated information system for use in a healthcare institution for analyzing, optimizing, and standardizing bills of resources for a given medical procedure performed within that institution.

SUMMARY OF THE INVENTION

The above and other needs are provided by an information management system for producing a standard bill of resources based on a plurality of bills of resources where each includes a list of resources to be utilized in performing a procedure. Included is a general purpose computer system with storage means for storing information related to the bills of resources, processing means for processing instructions relating to producing the at least one standard bill of resources, display means for presenting the standard bill of resources in a human perceptible format, and input means for receiving user input relating to producing the standard bill of resources.

Information management software is installed on the general purpose computer. Node software objects each provide a health care information management function. A clinical pathway node software object selectively creates, manages, and maintains user defined, user configurable clinical pathway module software objects adapted to function with the clinical pathway node software object, and represents provider specific procedural templates of the information relating to health care services procedures.

The clinical pathway module software objects include resource software objects that correspond to resources to be used in providing health care services. This includes the bills of resources that includes the list of resources to be utilized in performing the procedure. The clinical pathway modules software objects also include container software objects for containing software objects having at least one common characteristic.

A case management node software object selectively creates, manages, and maintains a user defined, user configurable case management module software object from the clinical pathway module software object. The case management module software object is adapted to function with the case management node software object. The case management module software object represents a selected clinical pathway module software object as modified to reflect a prospective patient specific case, and contains patient specific information. The case management module software object is also adapted to receive additional patient specific information.

A bill of resources standardization review node software object selectively creates, manages, and maintains a user-defined, user-configurable model module software object from the case management module software object. The model module software object is adapted to function with the bill of resources standardization review node software object. The model module software object represents a case management module software object as modified by at least the patient specific information to reflect a historical patient specific case. This is accomplished by selecting selected bills of resources from the plurality of bills of resources, and developing models corresponding to the selected bills of resources, where the models include values which correspond to a number of units of given resources from the selected bills of resources. The models are manipulated mathematically to highlight similarities and dissimilarities of defined characteristics in the models. The manipulated models are expressed in a format in which a relative position of each of the manipulated models may be determined, where the relative position of each of the manipulated models reflects the degree of similarity or dissimilarity to the other manipulated models. The selected bills of resources are analyzed based upon the expression of the manipulated models, and the standard bill of resources is produced based on the analysis of the selected bills of resources.

BRIEF DESCRIPTION OF THE DRAWINGS

The foregoing embodiments of the present invention may be best understood with reference to the following Detailed Description of the Preferred Embodiments and the drawings in which:

FIG. 4 depicts a model developed in accordance with a preferred embodiment of the present invention;

FIG. 5 depicts a matrix prepared for use in accordance with a preferred embodiment of the present invention;

DETAILED DESCRIPTION OF THE PREFERRED EMBODIMENTS

Figure 1:
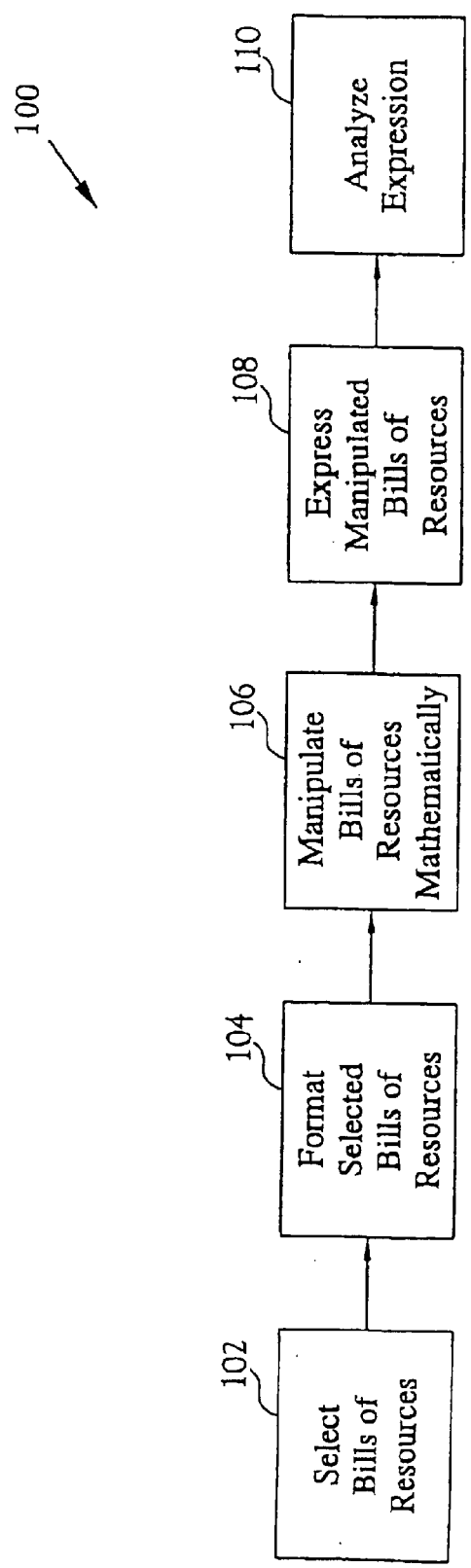
FIG. 1 is a block diagram of a preferred embodiment of the method of the present invention.

Considerable cost savings in the medical and other fields could be realized if there were an automated and convenient method for analyzing and optimizing resource allocation and usage. For example, it is known that doctors typically express strong preferences with respect to a relatively small number of supplies to be used during a surgical procedure. However, hospitals have typically used doctor preference cards as a whole bill of resources and, when given a choice, doctors will select a product with which they are familiar. Thus, there are often substantial chances to standardize or optimize preference cards for items about which doctors do not have strong preferences. Also, some doctors, because of a lack of historical information, will overbook other resources such as anesthesiologists, equipment, etc. just to make sure that the resource is available when needed; although, with good resource usage analysis, the doctor would be willing to standardize the scheduling of such resources.

The benefits of standardized bills of resources are varied and complex. With respect to supply standardization, enormous cost savings are available if supply consumption is standardized. The health care facility, supply distributor and manufacturers, when bills of resources are optimized, can benefit from inventory reduction, economies of scale, increased certainty in supply and demand, utilization of just-in-time manufacturing, shipping and inventory techniques, etc., because of the enhanced certainty of which supplies will be required. Furthermore, from the standpoint of the health care facility, the efficiency in the usage of labor and equipment resources can be increased by standardization by eliminating unproductive time and having a more certain knowledge of when labor and equipment resources will be required and used. Such knowledge will allow for more careful planning in the acquisition, training and utilization of such resources.

Almost any procedure may be described in the context of a procedural pathway; i.e. a series of related events, or sub-procedures, which are steps in the completion of a given procedure. A procedural pathway may be very general or extremely detailed. For example, with respect to a procedure such as changing a jet engine, the procedure could be generally described by the pathway: 1) prepare airplane, 2) remove old engine, 3) install new engine, 4) test airplane. Obviously, each of the steps described above entails much more detail work than is present in the pathway. However, starting with a general pathway, each step can be broken down into increasingly more complex and detailed pathways until, at the greatest level of detail, an explicit step by step process is described for each activity required to complete the procedure. Basically, the procedural pathway concept provides for a ready methodology for describing and analyzing how procedures are performed and understanding what is required to perform the procedure.

A bill of resources is simply a list of materials, equipment, personnel, supplies, facilities, etc. that are required in order to allow a procedure to be completed. In the example above, the bill of resources would include, among other things, a new jet engine, tools, mechanics, a hangar, scaffolding, engine test equipment, aircraft inspectors, test pilots, etc. A comprehensive bill of resources allows for the most efficient performance of a procedure since it will insure that all the required resources are available at the appropriate time. In fact, if the bill of resources is developed in conjunction with a procedural pathway, or is organized along the lines of a procedural pathway, the performance of the procedure is greatly enhanced since it will then be known just what resources are required and when, thus minimizing the amount of required materials and supply inventory and reducing the risk that labor and equipment resources are idle while waiting for other steps in the procedure to occur.

A very detailed description of the use of procedural pathways and bills of materials based thereon for use in an integrated medical supply system is described in U.S. Pat. No. 5,682,728 entitled Method For the Supply of Medical Supplies to a Health-Care Institution Based on a Nested Bill of Materials On a Procedure Basis. Also, the concept of building bills of resources and tracking resource utilization is described in U.S. Pat. No. 5,991,728 entitled Method and System for the Tracking and Profiling of Supply Usage in a Health Care Environment. The entire disclosures of these patents are hereby incorporated by reference thereto as if set forth fully herein. Use of the procedural pathway concept provides a convenient method for the construction of bills of resources for various procedures.

As discussed previously, one problem with bills of resources is that even within an organization, and for a given procedure, multiple bills of resources may be used. There are a variety of reasons that the different bills of materials may be required: the subject of the procedure may vary, different people performing the procedure may have different preferences, different but similar procedures are being performed, etc. Obviously, the extreme, ideal situation (from a standardization point of view) would be that for an organization, only one bill of resources would be used for all procedures, regardless of variations. This singular bill of resources would provide complete standardization (i.e. would include all resources which would be used in any procedure) and allow for predictability in inventory control, labor management, equipment purchasing and maintenance, etc. However, the cost of such a comprehensive bill of resources would be prohibitive because a lot of waste would likely be present. In order for the bill of resources to be comprehensive, the resources required for any variation of the procedures performed by the organization would have to be included, even when those resources would only be used a fraction of the time. Obviously, some middle ground must be reached between standardization of bills of resources and customization of bills of resources.

Turning now to the context in which this invention was developed, but not limited thereto, health-care facilities are an arena where bills of resources for various procedures are developed. In the context of the above general description, there are many opportunities for standardization in the medical field. For example, in a hospital stay, some patients will go through identical steps in a procedural pathway, regardless of what the medical condition of the patient is. All patients will be admitted, have certain bloodwork done, be issued certain identification and supply items. Thus, regardless of whether the patient is in the hospital for a heart bypass operation or to have a facelift, there is some degree of standardization of the bill of resources for both procedures that can be made.

For example, in the admission process, the bill of resources is likely to include certain forms that must be filled out, certain labor resources who take the patient information, date entry labor, identification supplies such as wrist i.d. bracelets, etc. Similarly, the baseline bloodwork is probably the same for nearly all patients and would require a labor resource for collecting the blood, certain supplies such as blood collection kits and vials, laboratory resources, etc.

However, as different procedural pathways continue, or even as identical procedural pathways directed to different patients continue, at some point the pathways diverge, at which point lock-step standardization is not only inefficient, but is detrimental. In the past, in order to enhance efficiency, hospitals had attempted to standardize supply ordering by negotiating pricing through group purchasing organizations, which would contract with a particular supplier in order to get the best price for certain types of medical supplies. Another solution was to utilize unitized container systems which attempted to minimize hospital inventory requirements (but typically which did not assist in optimizing standardization of bills of resources). Also, hospitals would use O.R. scheduling software to arrange for the use of equipment and labor resources during a given procedure. However, such systems were not integrated and could not select the ideal bill of resources for a given procedure. In fact, such attempts typically result in standardization at the expense of efficiency; i.e. often the use of supplies which are not preferred by care givers is dictated by the group purchasing contract and, while the software helps predict demand for OR's equipment and labor resources, they cannot help analyze the utilization of such resources and optimize the availability of such resources.

For ease of reference herein, each bill of resources to be analyzed in accordance with the present invention is referred to herein as a "model", and each item listed in the bill of resources is referred to as a "resource." Typically, resources will be a supply, a labor resource, a facility or a piece of equipment; thus, a resource could be a suture tray, a scrub nurse, an operating room, or a heart lung machine.

In the provision of medical services, one way of describing the process by which medical services are provided is through the concept of a clinical pathway. Any given treatment regime or clinical procedure, may be easily described as a related series of care events. Each care event has a some relation to the preceding and/or following care events that is logical and reasonable. For example, take a simple procedure such as suturing a wound. The task of suturing a wound can be described as a series of care events: 1) examination of the wound; 2) cleansing of the wound; 3) anesthesia; 4) suturing of the wound; and 5) dressing the sutured wound. Thus, each of these related care events, make up a clinical pathway for the procedure of suturing a wound. To a person familiar with the medical environment, it will be apparent that each of the care events could be broken down into a more detailed series of sub-care events, thus, the concept of the clinical pathway is scaleable; that is, any given care event may be made of a series of care events and can therefore be described as a clinical pathway.

The concept of the clinical pathway may also be expanded to more involved procedures. For example, a patient might go to her doctor complaining of particular symptoms. The doctor might then make an examination, or order tests.

Based upon the result of the examination and/or tests, the doctor would make a diagnosis and prescribe a treatment regime. Assume that the treatment regime included a surgical procedure to be performed in a hospital, as well as follow-up care. In this case, the clinical pathway might look like:

1) patient induction (basic administration getting the patient into the doctor's system); 2) examination; 3) testing; 4) diagnosis; 5) prescription of treatment; 6) admission to the hospital; 7) pre-surgical testing; 8) pre-operative preparation; 9) anesthesia; 10) surgery; 11) post-operative recovery; 12) discharge from hospital; 13) follow-up treatment; 14) final discharge.

Once again, it is obvious that each care event in the given example might be further broken down into smaller incremental care events and, thus, represent a clinical pathway of its own. For example, the surgery could be broken down into each step associated with the surgery from the initial incision until the incision is closed.

In addition to the fact that each care event represents the provision of some type of medical (or administrative) service, each care event will also require the allocation of some type of resources in order to be performed. These resources may be in the form of labor (doctor, nurse, technician, data clerk, etc.), equipment (x-ray machine, respirator, vital signs monitors, etc.), or supplies (sponges, surgical instruments, drapes, x-ray film, sutures, medications, etc.). Thus, for each care event it is possible to identify the allocation of resources necessary for completion of the care event. For example, for the examination step described in the second example, the allocation of resources could be: 15 minutes of doctor's time, use of a specimen collector, use of a specimen container, and the use of a blood collection kit. Likewise, the testing step might include the use of an imaging device (such as an x-ray or MRI machine), 30 minutes of technicians time, use of x-ray film, use of an x-ray developer and associated chemical supplies, and 15 minutes of a radiologist's time to interpret the images.

By describing events in the context of a procedural pathway, a framework is provided which allows for the systematic classification of the steps necessary to treat a particular patient as well as identifying the resource allocation necessary to properly complete the clinical pathway. In the current healthcare environment of cost control and containment, the use of the clinical pathway framework provides an effective and efficient method for characterizing and analyzing the provision of health-care services in the clinical environment.

Information systems in the health-care environment have used the paradigm of the patient record in managing information. That is, the primary identifying feature was the patient for information which was stored about resource allocation, supply utilization, resource scheduling, supply ordering, cost accounting, etc. Obviously, this paradigm has worked for some time owing in large part to the fact that cost reimbursement is done on a per patient basis, and all cost recovery and accounting needed to be allocable to an individual patient.

However, as health-care reform debate has forced health-care providers to focus on streamlining the provision of medical services, the focus has turned from patient-centered information systems to procedure-based management and accounting. Basing an information system around the procedural pathway, as opposed to just tying services, supplies and other resources used to the patient, with no real relation to the pathway, provides an inherent ability to use the information more efficiently and to allow for greater cost accountability in the provision of medical services.

To illustrate the efficiency of the procedural pathway, it is best to analyze generally a hospital stay for a given patient. Initially, the patient will be admitted, have some blood work done, be assigned a room, possibly be subject to some diagnostic screenings, possibly have a procedure done, spend a period of time recovering from the procedure and be discharged. Also, the clinical pathway may extend beyond the hospital stay and include follow-up care such as periodic check-ups and/or rehabilitation. Each step along the procedural pathway can be broken down into increasingly fine detail as series of more and more detailed sub-procedures. For example, the surgical procedure can be further broken down into surgical prep, anesthesia, the surgical procedure, closing and post-op anesthesia recovery. Obviously, each of these sub-procedures could be further broken down into specific tasks to be performed at each stage.

As can be seen from the procedural pathway model, each stage of the procedural pathway is going to require the utilization of resources. These resources may be labor resources, consumable supply items, durable equipment, reusable supply items, particular rooms (i.e. patient rooms, Operating Rooms (OR's), recovery rooms, etc.) or services. For example, the blood work will require a technician to draw the blood, the disposable equipment for drawing blood, a labor resource to deliver the blood to the laboratory, the consumable and reusable supplies for handling and testing the blood, durable medical equipment for testing the blood, labor resources for testing the blood and generating the report, and a labor resource for providing the report to the patient's chart. As can be seen, each resource can be analyzed and tied to a particular care event along the procedural pathway.

Each procedural pathway is going to have some unique characteristics which will vary based upon the reason the patient is in the health-care facility (the type of procedure), the doctor performing the procedure, and the characteristics of the patient. Obviously, the clinical pathway is different for someone having heart-bypass surgery than it is for someone having out-patient orthopedic surgery. Likewise, preferences vary from one doctor to another in performing the same surgery; i.e. one doctor may prefer the feel of one brand of scalpel while another doctor may prefer another. Finally, the patient often dictates variation within a given procedure; i.e. one patient may have certain physical characteristics that require using certain supplies and equipment and another patient may require different supplies and equipment.

The present invention provides an information system for use in the health-care environment that utilizes the procedural pathway paradigm for the input of data, the organization of data, the retrieval of data and the analysis of the data. In addition to storing unique data for each clinical pathway (historical data), the present invention also provides for the development of clinical pathways for certain medical procedures which have been analyzed and standard pathways developed. These clinical pathways, which are created from modular software objects configured by the user of the software, associate the anticipated resource allocation to a given procedure and allow for the anticipation of resource consumption for each upcoming standard procedure. For example, if a clinical pathway has been developed for a hip replacement surgery, the clinical pathway for a given patient coming in for hip surgery is easily developed from the template. The information system user would merely need to enter the identifying information about the patient and the surgeon performing the procedure, and the standard template would generate a clinical pathway showing the resources that should be required for that patient. At a further level of detail, departure points from the standard template can be identified and the alternate resource allocation for the departure points may also be provided in the information system. For example, this feature may be described as a conditional bundle. For example, in the hip replacement surgery described above, variations in resource requirements may vary from doctor to doctor because of differing techniques, requirements, and subjective preferences. Thus, the standard template for a hip replacement surgery may be substantially the same for two different doctors, but vary on a few items. The conditional bundles can be used to account for the departure from the standard template for each doctor and, by entering the doctor performing the procedure, the information system can automatically associate the appropriate conditional bundle with the standard template to form the clinical pathway for a given patient.

In terms of resource management, there are two basic types of resources which will be needed to perform a medical procedure at a given location: (1) those resources which will need to be brought in from outside the location for the procedure, and (2) those resources which are maintained by the location and which must be scheduled for a given procedure. For the purposes of this application, although doctors are not usually employed by the hospital, we will assume that they are resources associated with the location, since they are typically driving the scheduling of a procedure at a location. The management of outside and inside resources requires the consideration of two different sets of problems. Typically, the outside resources will primarily include the supplies which must be ordered from outside vendors, be delivered to the location, and be provided at the appropriate time and place for the performance of the procedure. The inside resources will include the labor resources, equipment owned and maintained by the location, and facilities at the location such as OR's, radiology, laboratories, etc.

In managing the outside resources there are two competing interests: (1) the desire to have sufficient quantities of everything readily available, which would necessitate a large inventory of supplies along with skilled personnel to maintain the inventory and deliver it for performance of the procedure, and (2) the desire to minimize inventory, which minimizes inventory carrying costs, the risk that inventory will expire before use, tied-up capital, and the skilled labor necessary to maintain the inventory and pull it for each procedure.

In managing inside resources the goal is to maximize the utilization of each available resource while carrying only the minimum amount of required resources to get the job done. Management of these resources necessitates that efficient resource allocation tools be used so that the location is not carrying costs associated with labor, equipment and facilities which are not being fully used, while insuring that all of the procedures can be performed in a timely fashion. For example, idle employees, equipment, OR's, etc. all carry a substantial cost. However, overworked employees, overused equipment and overbooked facilities reduce the efficiency and efficacy of the performance of the procedures and result in additional costs. Thus, precise scheduling and resource utilization management software is necessary to allow for the maximum productivity from resources, while minimizing inefficiency caused by overbooked resources and overworked employees. Additionally, software which allows for the detailed analysis of historical resource utilization will allow for the prediction of when new labor and other resources will be needed, and will provide for the most effective way of acquiring those resources, often saving money as opposed to the last minute recognition and rush acquisition of such resources.

DESCRIPTION OF THE PREFERRED EMBODIMENT

The preferred embodiment of the information management system consists of a series of software objects implemented using Microsoft ActiveX controls which may be configured and linked by a user to build a custom-configured health-care information management system. Preferably, the information system is implemented on a Windows NT or Windows 95 based personal computer, which may or may not be networked. In order to maintain a database of information related to this information system, a database program such as Microsoft SQL/Server or Microsoft Access is used in the background. The information system of the preferred embodiment generates data and communicates through an interface compatible with the background database program. Typically, the software objects which are described are coded in Visual C++ or Visual Basic, and adhere to the framework of ActiveX or OLE controls so as to maintain the ability to be implemented as compatible software objects in a component-based software architecture.

In general, the software provides a number of "nodes," each of which corresponds to a particular function of the information system. For example, if the system has functions for developing and maintaining software based clinical pathways, maintaining and logging resource consumption on a case by case basis, and studying resource consumption for logged cases, each of these functions represents one node. Each of these nodes uses the feature of ActiveX controls to allow objects created in one node to provide necessary information or form the basis for a new object in another node. The interaction of objects from one node to another will be described more fully hereinafter.

Figure 8:
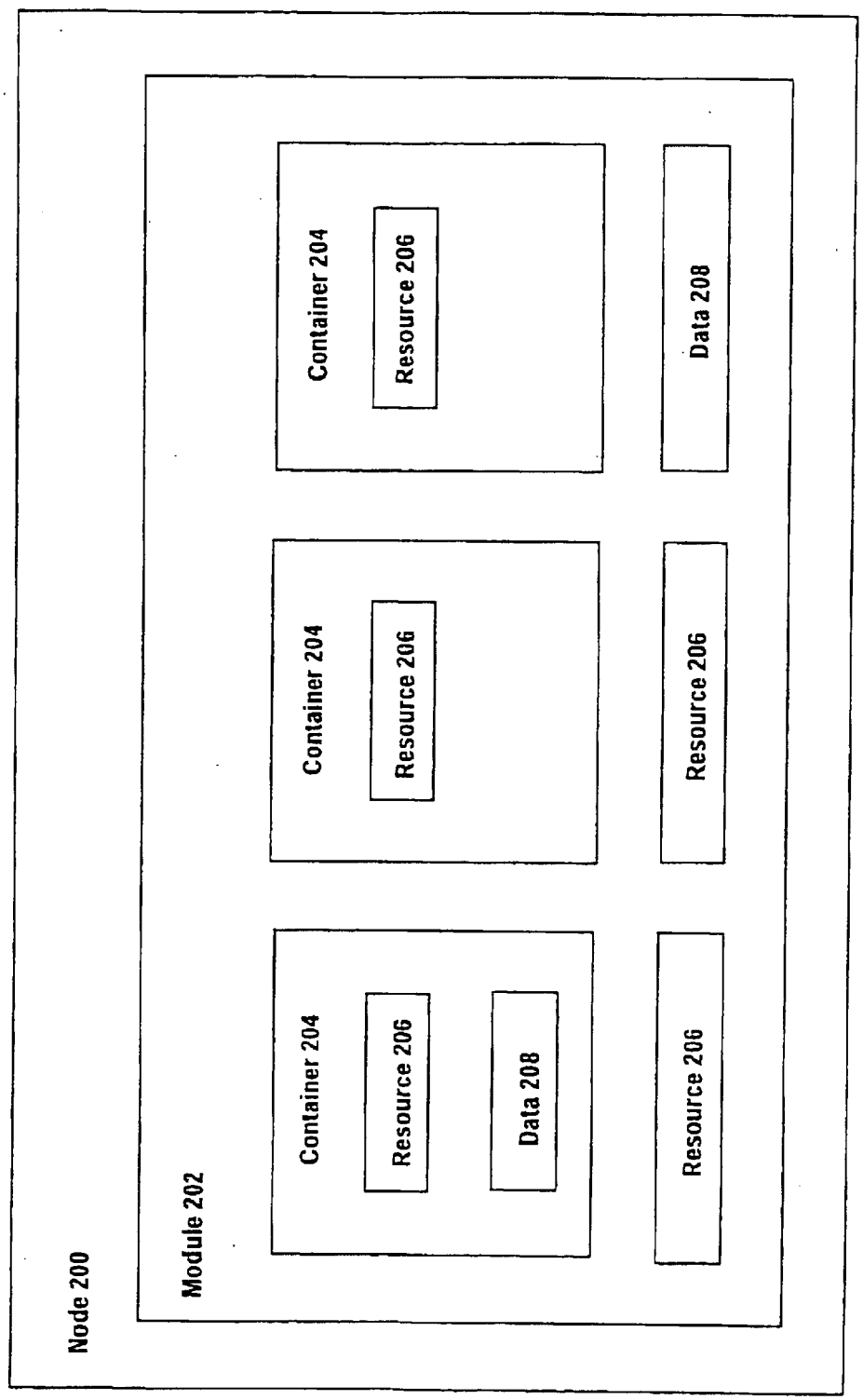
FIG. 8 is a block diagram showing a generic form of the present invention.

Referring now to FIG. 8, each node 200, as described, provides for a particular information management function in the present invention. Also, each node 200 represents a software object which will allow the user to perform certain functions and tasks relative to the information system function provided by the node 200. In general, the function of each node is to allow the user to generate specific templates, or software object modules 202 which organize additional software objects into custom configurations representative of the information to be managed. Under each node 200, the user has access to further software objects, or by copying from previously generated templates, by creating the objects or from an object library, in order to access the functionality of the node 200. The software objects available to the user are preferably of three specific types: (1) container objects 204, (2) resource objects 206, and (3) data objects 208. Each of these objects represent ActiveX software objects which function as miniature software programs to perform a specific function. Container objects 204 function as receptacles of other objects and act to organize the other objects in accordance with the user's specifications. Additionally, container objects 204 are customized by the input of data from the user based upon what the container object 204 is designed to hold, the specific use to which the container object is subjected by the user, and other usage specific data which the user provides.

Resource objects 206 are software objects which represent resources to be utilized in the provision of the healthcare. Resource objects 206 typically represent supplies, or kits of supplies, equipment, personnel, pharmaceuticals, or any other resource which will be utilized during the provision of health-care. Each resource object 206 is populated with data relevant to that object and communicates that information as required.

Data objects 208 are software objects that are used by the user to collect specific information for use by the template or the information system. For example, it may be necessary to gather certain procedure-specific information at some point in a clinical pathway, and a data object 208 may be inserted at that point in a module 202 to collect such data and make it available to the appropriate software objects.

Figure 9:
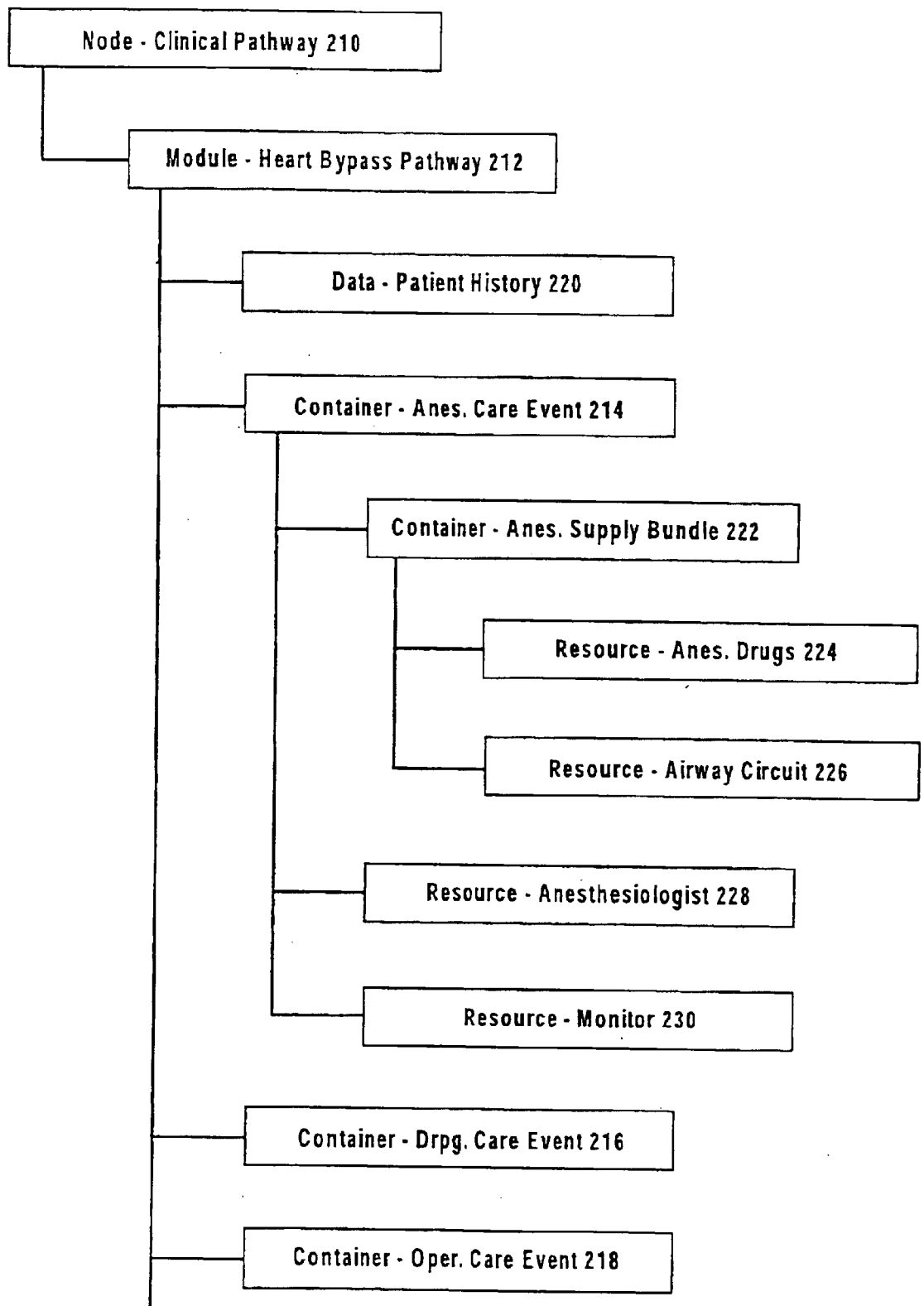
FIG. 9 is a tree diagram showing the organization of a preferred form of the present invention.

Use of the software objects is best understood by a general reference to one function of the information system. Referring now to FIG. 9, the first node 210 of the software represents the function of generation, modification, and maintenance of software templates for clinical pathways using the objects previously described. This node 210 allows the user to create software modules 212, made up of user selected objects, which represent in software a health-care procedure or clinical pathway. In general, as described previously, the clinical pathway is broken down into a series of related care events, representing discrete sub-procedures along the clinical pathway. Using the functionality provided by the clinical pathway node 210, the user is able to develop a new module 212 by making the appropriate menu selection. The user is prompted to input information relevant to the clinical pathway generally, such as the name of the clinical pathway, any hospital or other codes used to identify the type of procedure, doctors who perform that type of procedure, etc.

Once the module 212 is defined and created, the user breaks the procedure down into a series of care events. For example, if the procedure is a heart bypass operation, various care events can be identified such as (1) anesthesia care event, (2) draping care event, and (3) the operative care event. Each of these care events are implemented in the clinical pathway module 212 by the selection or creation of care event container objects corresponding to each care event 214, 216, and 218. These objects require the input of information relevant to the care event and function as containers for additional container, resource, or data care events.

Once the care event containers 214, 216, and 218 have been created in the module 212, the user fills out each of the associated care events for the module. For example, a patient history data object 220 might be associated with the module 212 which prompts the user to obtain patient-specific data when the clinical pathway is used relative to a particular patient. Resources are then associated with each care event.

For example, the Anesthesia Care Event container 214 may contain an anesthesia supply bundle container 222, which in turn can contain resources such as anesthesia drugs 224 and an airway circuit 226. Other resources, provided by a resource object, such as an anesthesiologist 228 and patient monitor 230, are also associated with the anesthesia care event 214. In the example, the anesthesia drugs resource 224 represents a pharmaceutical resource object, which contains certain information relevant to the specific drugs to be delivered, while the airway resource 226 represents specific supplies to be used in the anesthesia care event 214; these two items, because they will be used together, are combined in a supply bundle container 222 which may be reused for other procedures which include an anesthesia care event. The anesthesiologist resource 228 represents a personnel resource object, and contains information concerning the anesthesiologist including identification, time to be allotted for the procedure, and scheduling information. The patient monitor resource object 230 represents an equipment resource, which contains information about its availability and utilization.

This process is repeated until each of the remaining care events 216 and 218 for the clinical pathway is complete. The user of the information system then has a software module 212 configured for the heart bypass clinical pathway which consists of container, resource and data objects. Each of the software objects encapsulates information particular to that object and communicates that information via a standard interface to other software objects as such information is required.

For example, after constructing a particular clinical pathway module, the user might desire to schedule a procedure for a particular patient using the clinical pathway. By utilizing a node designed to manage information for individual cases, the user selects the appropriate clinical pathway module which transfers the data from the clinical pathway module for that procedure into a case module. The case module then contains all of the information from the objects from the selected clinical pathway module and provides a ready listing of resources to be utilized in performing the procedure. With this information, schedules of supplies, equipment, etc. are generated in order to facilitate the performance of the procedure.

Additionally, as is described more fully hereinafter, by creating a case module, the user has available the case node functionality which allows for the tracking of resource utilization in performing the procedure, creating a consumption record for use in analyzing resource utilization, generating cost information for cost recovery, and other case node specific functions. Also, to the extent that objects created in the clinical pathway have utility for other clinical pathways, the created objects may be reused to develop additional clinical pathways.

As described in greater detail below, the various types of objects are predefined in the overall software system. Container objects are available to represent care events, supply bundles, and conditional supply bundles. Each type of container may be configured by the user to reflect the particulars of the clinical pathway to be represented. Care event containers are configured with specific information for each care event in the clinical pathway and contain information relevant to that care event. Supply bundles are provisioned with supply resource objects and have information specific to that supply bundle contained therein. Conditional supply bundles are provisioned with supplies and a condition which will determine if that conditional supply bundle will be used. For example, a conditional supply bundle developed for a particular surgeon has supplies used only by that surgeon provided therein. If the condition is met when a case is scheduled, such as the particular surgeon is assigned to the case, that conditional bundle is automatically added to the list of objects associated with that case.

Similarly, various types of resource objects are provided as standard templates for configuration by the user. Examples of such types of resource objects are supplies, kits (which are pre-packaged groups of supplies), equipment, personnel, and pharmaceuticals. When configuring resource objects for a clinical pathway, the user selects the appropriate supply type for the resource to be represented, and inputs the prompted information. For example, the user might be able to look up a database of listed supplies and select a particular supply for inclusion in the clinical pathway.

Alternatively, the user could create a new supply from scratch by inputting prompted information to create a new supply resource object. The type of information varies from resource type to resource type, but a standard template is provided for each resource type to prompt the user to input the appropriate information for each resource to be added.

Additionally, while the user has the option to create various container, resource, and data objects from scratch for use in the information system, the user, to the extent appropriate, would be able to reuse previously created objects. For example, the user might create a library of standard pre-configured objects which are frequently re-used in various clinical pathways. Thus, when a new pathway is created, these library objects may be selected for inclusion in the new pathway. Likewise, information concerning a variety of resources may be maintained in various database systems maintained by a health-care institutions. The supply department may maintain a database of available supplies, or dealers may provide databases of available supplies, by providing standard database program interfaces for these sources of information, data from these sources may be automatically read into the present system in order to configure resource software objects for use therein.

As described, the use of software objects to represent events, bundles, resources and data objects in a health-care information management system allows the user to readily create software modules which represent specific health-care procedures, which are much more functional than with traditional health-care database systems. Furthermore, the module object approach to the system makes it more readily customizable for particular installations. For example, if the standard configuration of any software object is not readily adapted for a particular installation, a programmer is not required to modify a monolithic source code listing to implement the new configuration. For customization, the programmer preferably rewrites the code only for a particular object. As long as the programmer retains the standardized data interface for the object, there is no need for any change in configuration in the remaining source code for the system.

Additionally, the use of the software object framework allows for the ready implementation of new functionality, without requiring the rewrite of the majority of the code for the system. For example, if a new functionality is required, a new functional node may be added which utilizes, to the extent possible, already existing software objects.

The preferred embodiment of the present invention adds such new functionality by introducing a bill of resources standardization node software object to the above-described software to provide for creating a standard bill of resources based on a number of existing bills of resources. Most of the bill of resources information for any given procedure is available in the clinical pathway module for that procedure. Thus, to create the bill of resources standardization node, the programmer creates a software object that queries existing software objects for information relevant to bills of resources, and that analyzes that information as described below to identify standardization opportunities. In implementing such a node, individual procedural pathways may be copied from a clinical pathway constructed as described above with reference to FIG. 9.

Referring now to the block diagram of FIG. 1, a preferred method of implementing the bill of resources standardization node is described in more detail. The first step 102 in carrying out the present invention, is selecting the bills of resources for which analysis or optimization is to be performed. Although this step may seem trivial, it is in fact very important. For example, the goal may be to find a standard bill of materials for a given type of medical procedure, such as a total hip replacement. In that case, the bills of materials for all total hip replacement surgeries needs to be collected. In another situation, it may be desired to analyze resource utilization for all procedures done in the hospital to identify similarities and differences. In that case, bills of resources for all procedures performed by the hospital needs to be acquired. Finally, in another situation, it may be desirable to determine how consistent a single doctor is in terms of resource utilization. In that case, a bill of resources for all procedures performed by that doctor needs to be acquired.

After the desired bills of resources are accumulated, the second step 104 is to format the bills of resources into a format in which the bills of resources can be manipulated mathematically. Again, this step may seem trivial, but given the complexity of a bill of resources for even a simple procedure, the manner in which the information is formatted becomes important. As described in detail below, the preferred format for this step 104 is a matrix in which each column is a model and each row is a resource. Thus, the matrix has a width equal to the number of models to be analyzed and a length equal to the total number of different resources present in all of the models. The actual numbers present in the matrix is the number of units of a given resource present in a given model. Optionally, it may be desirable to include other information such as the aggregate cost of that resource or historical information on the number of units of that resource actually used instead of the number of units provided in the bill of resources. Thus, it should be apparent that with even relatively simple bills of resources (models), the matrix built from the models is very complex.

The third step 106 is to manipulate the matrix mathematically in order to highlight the similarities or differences of the various models analyzed. In the case of the preferred embodiment described herein, the mathematical manipulation involves the manipulation of the matrix using matrix factorization and rank reduction techniques to reduce the number of scalar values representing each model to two or more. In effect this reduces the number of values representing the model from a large number equal to the number of rows in the original matrix, to a smaller number of values which can be more easily analyzed.

The fourth step 108 is to express the manipulated models in a format in which the relative position of each of the models may be determined. The expression of the manipulated models allows analysis to be done with models having a dimension equal to the total number of resources across all the models (a very large number) in a format in which the dimension of the expression is more manageable. For example, if there are a total of 300 resources listed in the models to be analyzed, then the number of rows in the matrix expression of those models is equal to 300, and the analysis of the un-manipulated matrix needs to be analyzed in 300 dimensions. Obviously, the analysis of a problem in 300 dimensions is very difficult, even with computer assistance. However, the expression of the manipulated matrix in a reduced number of dimensions makes the analysis of models much simpler.

Using the techniques described herein, the number of dimensions of the expressed model may be selected. If it is desirable to analyze the information on a two-dimensional plot, then the dimension of the expression can be selected to be two. If a three-dimensional projection is desired, then the dimension of the expression can be selected to be three. If a more complex expression for computer analysis is desired, some higher value for the dimension of the expression may be selected. The key attribute of the expression is that the large dimension required by the number of components of the bills of resources is reduced to a more manageable level, while still retaining usable information about the relative similarity or dissimilarity of the models being analyzed.

The final step 110 in the method of the first preferred embodiment is to analyze the expression of the manipulated models. This analysis may range from measuring the distance between models to determine how similar or dissimilar they are, to attempting to group models by their degree of similarity for the purposes of developing standardized bills of resources for the grouped models. Another type of analysis is to compare proposed standardized bills of resources to actual bills of resources to measure the effectiveness of the standardization attempt. Also, this method could be used to analyze historical usage information from bills of resources reflecting actual usage of resources during procedures to find variations and deviations among similar procedures, or to identify similarities among disparate and distinct procedures.

As described herein, the technique utilized to manipulate the mathematical models 106, is preferably selected so as to highlight the desired similarities between the models. This selection is important to the functionality of the process, because improper selection of the manipulation technique could make the analysis useless. For example, the preferred matrix factorization technique described below is selected because it incorporates the 12 Norm (the matrix equivalent to a least squared error scalar calculation) which serves to highlight the similarities between models; i.e. after the manipulation, the most similar models, in the least squared error sense, have assigned numerical values that are similar. However, if an appropriate manipulation technique is not selected, the manipulation may highlight insignificant similarities or the assigned numerical values of the models will not reflect any useful comparative information.

Figure 2:
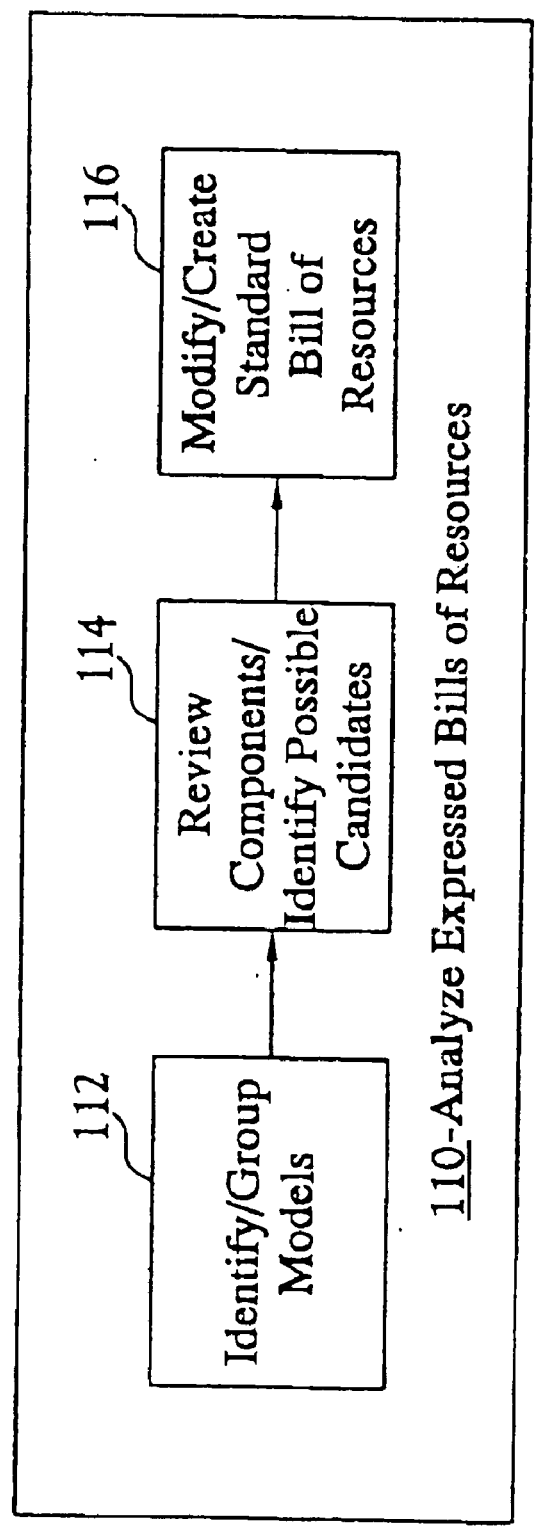
FIG. 2 is a block diagram showing additional steps of a preferred embodiment of the present invention.

Referring now to FIG. 2, additional steps associated with a further embodiment of the present invention are shown. This embodiment is an expansion of the analysis step 110 described in FIG. 1. In FIG. 2, the analysis takes multiple steps. The first step 112, is to identify clusters of relatively similar models as likely candidates for optimization or standardization. As will be described more fully hereinafter, the method of identifying similar models depends on the method used to express the manipulated models (108 of FIG. 1). For example, if the expression is a two-dimensional or three-dimensional graph, then a simple look at the graph may suffice to identify clusters of similar models. However, if the expression is in more dimensions, then computer analysis of the expression may be used. For example, regardless of the number of dimensions of the expression, a computer could be used to perform vector subtraction of the models relative to each other, and by selecting a threshold value, similar models may be defined; i.e. all models in which the vector difference between models is below some value could be considered similar. Also, various grouping/ clustering algorithms could be developed which serve to identify similar models based upon the expression.

Once the models are grouped/clustered 112, the next step 114 is an analysis of the individual components of the original bills of resources from which the models were generated. This component analysis 114 includes the identification of components which may be standardized among the various bills of resources, and can also be used to identify components which have an aberrational usage history in one or more bills of resources. This step 114 serves the purpose of identifying strategies for standardizing a bill of resources or modifying usage patterns in order to more efficiently select and provide resources for use during a procedure.

The final step 116 of FIG. 2 is the step of modifying one or more bills of resources in response to the previous described steps. This modification 116 can be linked to the identification of a standard bill of resources which is used in all procedures, or a portion of a bill resources is standardized with the remainder retaining differences present in the original models. Another form of modification 116 relates to the method in which one standardized bill of resources is selected. In some instances, it might be desirable to pick the one model which is the most similar to all of the other models as the standard bill of resources, and require that all of the other bills of resources conform to that one. In other situations, it might be that the bill of resources associated with the doctor that performs the largest number of procedures might be selected. In still other circumstances, a completely new bill of resources, which represents the greatest amount of similarity to the largest number of the analyzed bills of resources, might be developed. In yet another set of circumstances, the analyzed bills of resources might be actual usage histories (consumed resource lists) reflecting resource utilization in a given procedure or for a given doctor. In this case, the modification to the bill of resources may be made to more accurately reflect the actual usage patterns.

Referring now to FIGS. 3–6, a description of a preferred method for implementing the present invention is described. It should be noted that the preferred implementation of the invention is tied to the use of matrix and vector mathematics, and in particular to the techniques of matrix factorization and rank reduction. However, other matrix manipulation techniques might be used to achieve the results described below. Furthermore, although it is currently believed that due to the form of bills of resources, matrix and vector mathematics are the most readily apparent techniques for analyzing bills of resources, other mathematical techniques not limited to matrices and vectors could be used to analyze the information.

Figure 3:
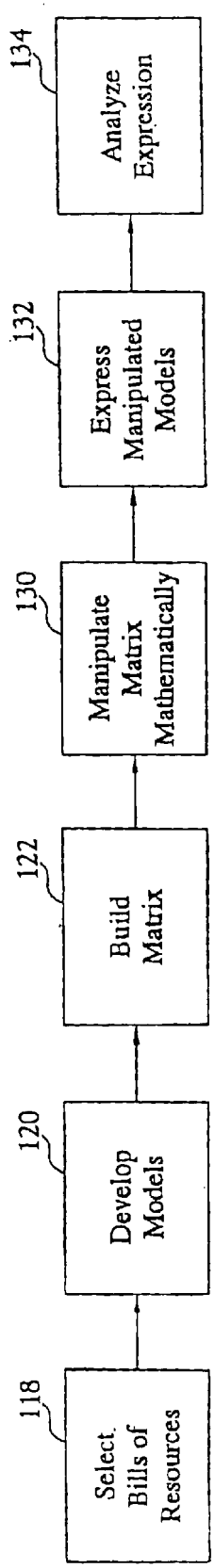
FIG. 3 is a block diagram showing an alternative embodiment of the method of the present invention.

Referring now to FIG. 3, the first step in the preferred embodiment shown therein is the selection of the bills of resources to be analyzed 118. This step 118, although it sounds basic, is important because the selection of the bills of resources must be consistent with the type of analysis to be performed. For example, if the interest is in developing standardized bills of resources on a procedural level, then the selected bills of resources are all those associated with a given procedure. However, if the desired analysis is to be used to look for standardization opportunities across all orthopedic procedures, then the universe of bills of resources are different.

Once the bills of resources to be analyzed have been selected 118, the next step 120 is to develop a model for each bill of resources. Referring now to FIGS. 3 and 4, there is shown in FIG. 4, a model based upon a bill of resources. Basically, the model is a table with a listing of all of the resources present in the subject bill of resources, with the number of units indicated next to each resource. Ultimately, the resource listing in each model will be identical and will be comprehensive across the models, and the differences will be in the number of units of each resource indicated for a given model. For example, if it is discovered that in a second or later model, there is a listed resource which is not included in the first model, then the first model is modified to include this resource, and the number of units of that resource for the first model will simply be zero. This process is repeated until the resource listing is comprehensive.

Once models have been constructed 120 for each of the bills of resources to be analyzed, a matrix 122 is constructed 122 in which the columns correspond to the models and the rows correspond to the resources. The matrix has a dimension of M×N, where M is the number of resources across the models and N is the number of models. There is shown in FIG. 5 a sample matrix 124. This sample matrix has four columns 126 corresponding to four models and 63 rows 128 corresponding to a set of 63 resources across the models. As described previously, the individual numbers of the matrix identify the particular number of a given resource present in a given model.

Once the matrix is constructed 122, the mathematical manipulation 130 of the matrix is performed. In the preferred embodiment of the present invention, the matrix is factored and its rank reduced as set forth below.

Assume a constructed matrix $A \in R_{M \times N}$, $$A = [\underline{a}_1 \; \vdots \; \underline{a}_2 \; \vdots \; \cdots \; \vdots \; \underline{a}_N], \quad \text{Eq. 1}$$

where $a_n \in R_{M \times N}$, n=1 ... N represents a model, and the elements in $a_n$ are the resources of the $n^{th}$ model. Then the matrix A can be expressed using one of many matrix factorization techniques. One classical technique is known as Singular Value Decomposition (SVD), in which the matrix $A_{M \times N}$ is expressed as, $$A_{M \times N} = U_{M \times M} \Sigma_{M \times N} V_{N \times N}^T, \quad \text{Eq. 2}$$

where the matrix subscripts have been included to explicitly designate the dimension of each matrix. The columns of $U_{M \times M}$ are called left singular vectors, and the columns of $V_{N \times N}$ are known as right singular vectors. The matrix $\Sigma_{M \times N}$ consists of zeros with the exception of its main diagonal containing the singular values of $A_{M \times N}$. Matrix $A_{M \times N}$ is generally of full rank; that is, none of its singular values equal zero.

It is desired to represent the data matrix $A_{M \times N}$ in an r dimensional subspace. One method of accomplishing this is to express the columns of $A_{M \times N}$ as linear combinations of r vectors which span the desired subspace. In the following equations, r=2 is used for convenience, but in general $1 \leq r \leq \min(M,N)$. Thus $A_{M \times N}$ may be approximated by the rank 2 matrix $\hat{A}_{M \times N}$, $$\hat{A}_{M \times N} = [\alpha_1 \underline{b}_1 + \beta_1 \underline{b}_2 \; \vdots \; \alpha_1 \underline{b}_1 + \beta_{21} \underline{b}_2 \; \vdots \; \alpha_N \underline{b}_1 + \beta_N \underline{b}_2], \quad \text{Eq. 3}$$

where $b_1, b_2$ form a basis for $R_2$. The coefficient pairs $(\alpha_n, \beta_n)$ n=1 ... N are then used to represent each model in the two-dimensional space, aiding in further analyses of relationships among models.

The next step is determination of the coefficients $(\alpha_n, \beta_n)$, n=1 ... N. This is preferably done using information from a matrix factorization technique. In the case of the SVD factorization technique, one may employ a standard rank reduction technique to express $\hat{A}_{M \times N}$ as, where $\sigma_i = \Sigma(i,i)$, $v_{ij} = V(i,j)$, and $u_i = i^{th}$ column of U. This representation of $\hat{A}_{M \times N}$ is analogous to the desired representation with, $$\underline{\alpha} = \begin{bmatrix} \alpha_1 \\ \alpha_2 \\ \vdots \\ \alpha_N \end{bmatrix} = \begin{bmatrix} \sigma_1 v_{11} \\ \sigma_1 v_{21} \\ \vdots \\ \sigma_1 v_{N1} \end{bmatrix} = \sigma_1 \underline{v}_1, \text{ and} \quad \text{Eq. 5}$$

$$\underline{\beta} = \begin{bmatrix} \beta_1 \\ \beta_2 \\ \vdots \\ \beta_N \end{bmatrix} = \begin{bmatrix} \sigma_2 v_{12} \\ \sigma_2 v_{22} \\ \vdots \\ \sigma_2 v_{N2} \end{bmatrix} = \sigma_2 \underline{v}_2, \quad \text{Eq. 6}$$

where $v_i = i^{th}$ column of V, and $b_1, b_2$ corresponds to $u_1, u_2$. The preferred standard rank reduction technique is that described in *Matrix Computations*, Second Edition, Golub, Gene H. and Van Loan, Charles F., The Johns Hopkins University Press, Baltimore, 1989, at pp. 70–73, the text of which is incorporated by reference as if set forth fully herein.

By this mathematical technique, each model is expressed with two values $\alpha_i$ and $\beta_i$ (since the selected dimension was two). With each model now expressed as two scalar values, the models are preferably expressed 132 in a two-dimensional graph which visually highlights which models are similar and which are different.

Figure 6:
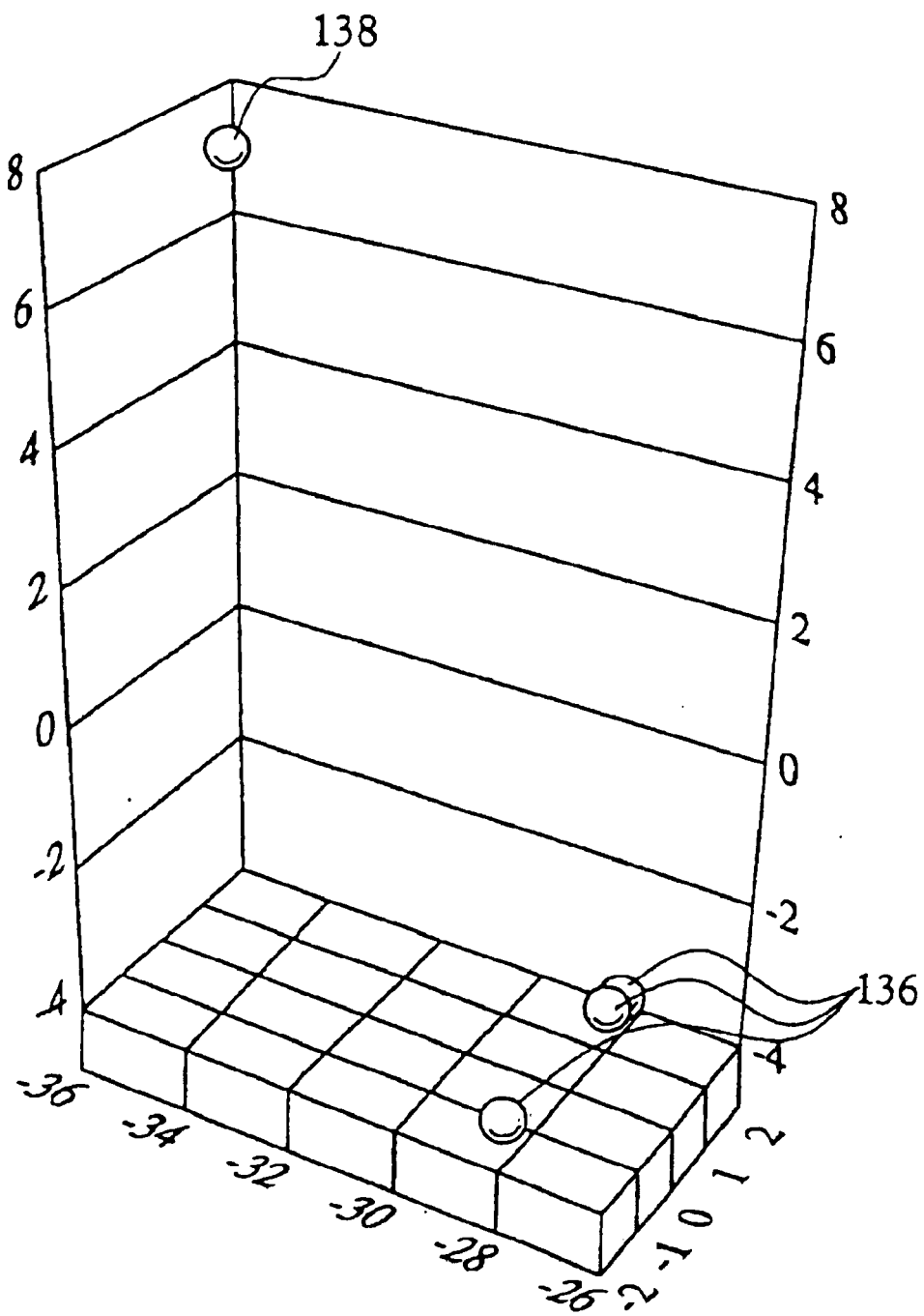
FIG. 6 depicts a graph generated in accordance with a preferred embodiment of the present invention.

Referring now to FIG. 6, a graph is shown for an actual set of models. The selected number of dimensions for the graph is actually three (as opposed to two, which was used in the development of the mathematical discussion above; to one skilled in the art, the substitution of r=3 for r=2 in the above described mathematical development is readily accomplished). For analysis on a hard copy graph, the preferred dimension is probably two. However, for viewing on a computer, the preferred dimension is probably three, since more information can be conveyed and the inherent display features of computers can be used to rotate the three-dimensional display to allowing viewing from various angles.

Regardless of the number of dimensions used to display the mathematically manipulated models, the next step 134 in the method of the preferred embodiment is to utilize the expression 132 to analyze the various bills of materials from which the models are derived. Probably the simplest form of analysis is to identify any aberrational models which are a relatively large distance from the rest of the models in the expression. For example, if the models represent the doctor preference cards of various physicians performing the same surgery, identifying an outlying model from the graph would allow the hospital to attempt to reform that bill of resources in order to bring that doctor's resource utilization more in line with the norm.

Alternatively, the models may represent actually-logged procedures for a single physician and the distances between the expressed and manipulated models may represent variations in resource utilization from one performance of a procedure to the next. This type of analysis allows for the care provider to identify areas in which variations may be minimized.

Figure 7:
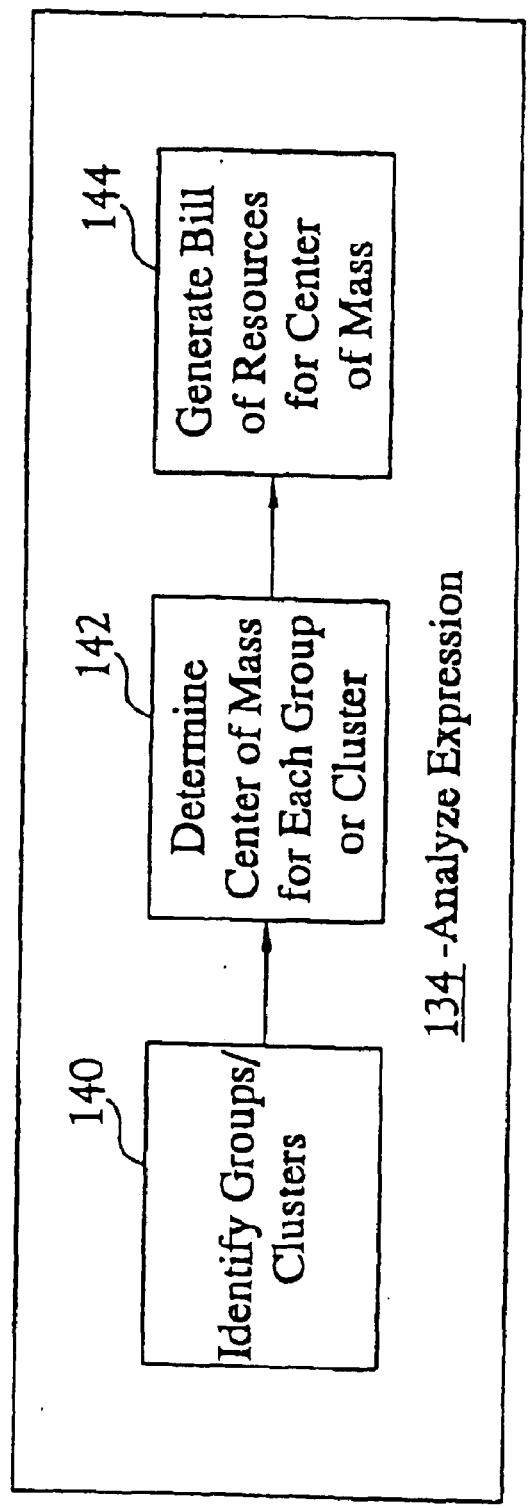
FIG. 7 is a block diagram showing the method steps of an alternative embodiment of the present invention.

As a more detailed form of analysis, the expressed information may be the basis for a more involved analysis as is $$\hat{A}_{M \times N} = [\sigma_1 v_{11} \underline{u}_1 + \sigma_2 v_{12} \underline{u}_2 \; \vdots \; \sigma_1 v_{21} \underline{u}_1 + \sigma_2 v_{22} \underline{u}_2 \; \vdots \; \cdots \; \vdots \; \sigma_1 v_{N1} \underline{u}_1 + \sigma_2 v_{N2} \underline{u}_2], \quad \text{Eq. 4}$$

described with respect to FIG. 7. As can be seen from the graph of FIG. 6, there will often be groups 136, 138 of expressed models which are relatively close to each other. These grouped models represent similar bills of resources. If the goal of the analysis is to replace multiple bills of resources (in the case of a surgical procedure, one doctor preference card for each doctor performing the procedure) with a smaller number of standard bills of resources, or even a single bill of resources, then the logical starting point is to identify the most closely related bills of resources, since standardization among the similar bills of resources may be accomplished with the minimum number of changes.

Alternatively, instead of performing the matrix factorization and rank reduction techniques, the various models are averaged on a row by row basis to develop a "best fit" model (i.e., the number of units of resources indicated in each row of the model are averaged or the mode or median calculated). This "best fit" model is then compared to the other models using any mathematical comparison technique, such as vector norms, correlation, etc. to determine how each model differs from the "best fit" model, and the degree of similarity or dissimilarity can be expressed as numerical values. While the factorization and rank reduction techniques provide the advantage that a graphic representation of the models can be generated more easily, and therefore that the degree of similarity of the models may be identified visually, the averaging technique results in an expression from which similarities among the models can be determined.

Referring to FIG. 7, a further embodiment of the invention is described. With respect to FIG. 7, the first step 140 of the method is to identify groups or clusters of expressed models (136, 138 from FIG. 6) which are relatively close together. The next step 142 is to identify a model which represents a "center of mass" of the cluster. This step 142 may be as simple as identifying an actual expressed model which is near the center of the cluster as the center of mass, or may be done by calculating the location of a model which would be the center of mass of the group or cluster. The final step of the method described in FIG. 7 is to generate a standardized bill of resources from the model representing the "center of mass" of each identified cluster or group of models.

In the preferred embodiment of the present invention, the center of mass (COM) of a cluster of models is calculated using a weighted average method. For example, each of the expressed models represents a bill of resources for a procedure being performed. However, some bills of resources are more important than others; it may be that one bill of resources is used more than others, or that one bill of resources is preferred by a more senior physician. In these circumstances, in addition to the data points associated with the expressed models in a cluster, each model is assigned a "weight" representing the relative importance of the model in performing the center of mass calculation.

Assume that a cluster for analysis included in a given study is comprised of N models. That is, there are N data sets (each data set=2 numbers for 2D, 3 numbers for 3D, etc.). It is desired that the average (center of mass) of the data cluster be determined in such a fashion that weighting is introduced. This weighting can be arbitrary or can be systematic in that, if each model represents a bill of materials (BOM) for a certain procedure, the relative importance of each model (BOM) can be determined by the number of procedures performed in a given interval. Arbitrary weighting can also be assigned in order to give preference to desired models.

The following is a numerical example of a study. Given a cluster of 5 models which are represented in 2D, they may be weighted as follows:

| Model # | Data Set (x, y) | Weights |
|---|---|---|
| 1 | (1.5, 3.7) | 25 |
| 2 | (2.0, 2.5) | 100 |
| 3 | (1.7, 3.0) | 400 |
| 4 | (2.5, 4.0) | 11 |
| 5 | (1.8, 2.7) | 30 |

In this example, each model represents a distinct BOM that is used for a medical procedure. The weights represent how many procedures are performed monthly. The 2D coefficients are determined based on the Matrix factorization approach described previously.

The weighted COM for a 2D data set would be calculated as follows:

$$COM = (\eta_x, \eta_y) \text{ where } \eta_x = \sum_{i=1}^{N} \alpha_i x_i, \quad \text{Eq. 7}$$

$$\eta_y = \sum_{i=1}^{N} \alpha_i y_i, \text{ and } \alpha_i = \frac{w_i}{\sum_{i=1}^{N} w_i}.$$

Thus, $\alpha_i$ is a percentage of the total weighting for the cluster being analyzed. For the numerical example given above, $\alpha_1$=25/566, $\alpha_2$=100/566, and so on. The weighted COM=(1.7650, 2.9461).

When calculating the standard deviation (STDEV) for the 15AKS cluster, the weighted COM is used. The STDEV formula for the x coefficients is given by, $$STDEV_x \frac{1}{N-1} \left[ \sum_{i=1}^{N} (x_i - \eta_x)^2 \right]^{\frac{1}{2}}, \quad \text{Eq. 8}$$

and likewise for the y coefficient. This two-dimensional development is easily extended into an arbitrary number of dimensions. For R dimensions, each data set contains R components. The COM has R components, and R STDEV components are obtained.

With the center of mass calculation performed, the generation 142 of the standard bill of resources is performed by substituting the calculated values into the matrix by substitution of the calculated center of mass coordinates into Equation 3 described previously. The center of mass values correspond to the $\alpha$ and $\beta$ coefficients for a new model, which are reconstructed as a complete calculated model. This action results in a un-factored model from which the bill of resources may be recovered. Alternatively, for a given cluster or group of similar models, one model may be selected as the standard for the cluster or group. For example, if one of the models is positioned near the center of the group, or if one model fits certain criteria such as lowest cost or most uses in a given time period, then that model may be selected as the basis of the standard bill of resources as opposed to conducting a center of mass calculation.

The preferred method of the present invention is implemented in computer software. For the purposes of inputting the information concerning the bills of resources, and displaying the information, a common database program is used. For example, for the model shown in FIG. 4 and the matrix shown in FIG. 5, Microsoft's SQL/Server software is preferably used in order to organize the data and display it. Other database programs, such as Microsoft Access, could be used as well. Additionally, to the extent that the information from the bill of resources is available from some other source, it could be imported in electronic form from another application. For example, DeRoyal's RCL™ software, described in U.S. Pat. No. 5,991,728, which is incorporated by reference, is a software package for managing bills of resources and resource consumption. In the preferred implementation of the present invention, the electronic version of a bill of resources is generated by utilizing that software.

Additionally, the mathematical calculations previously described are preferably implemented in software using RogueWave's math software (and could be implemented with a variety of software packages such as Matlab++, Mathematica, MathCad, etc.) which provided code in a C++ format. The remainder of the software was developed using C++ in an object oriented environment such as OLE or ActiveX. One skilled in the art will easily identify a variety of ways of implement the preferred method using various programming languages, operating systems, computer platforms, etc. The preferred environment is an object oriented programming language (such as C++) and a Microsoft Windows 95 or NT platform, using ActiveX or OLE controls and a client/server database such as SQL/Server.

The analysis of the bills of resources can be performed for a variety of purposes, including standardization or optimization of a bill of resources. As described above, depending on the bills of resources selected, the preferred embodiment allows a multitude of different questions to be asked concerning bills of resources. For example, as described, one primary use of the invention is to create a standard bill of resources for a given procedure in order to minimize deviations in usage and to maximize efficiencies of scale and distribution. However, by selecting bills of resources indicating consumption of resources during procedures, one can determine how supplies are actually being used and look for deviations in usage. Also, bills of resources can be compared to actual resource utilization to see how closely actual usage is predicted by the bill of resources in order to determine if the bill of resources should be modified.

Also, bills of resources from different procedures may be reviewed to identify standardization opportunities among different procedures. For example, many different medical procedures require utilization of many of the same resources. Thus, by using the present invention, opportunities for standardization of some items across many procedures could be developed. Items common to many procedures could be grouped and then a partial standard bill of resources for those components could be developed. In fact, this procedure could be repeated at various levels of the procedural pathway to develop levels of standardized bills of resources at each stage of the procedural pathway. For example, regardless of the procedure to be performed, a standard bill of resources may be able to be developed for admission to the hospital and, possibly, initial lab work. Then, depending upon the patient, a standard bill of resources could be developed for all surgical, OB, etc. patients. Then a standard bill of resources could be developed for all orthopedic surgical patients. Then a standard bill of resources could be developed for all knee surgeries. Then standard bills of resources could be developed for all knee replacement surgeries. This process could be repeated until strong doctor preference variations are reached (which would signal the end of standardization opportunities). The creation of a comprehensive bill of resources for a given patient would then entail selecting the appropriate standard bills of resources for each stage of the procedural pathway down to the individual doctor preference items. However, even though the bill of resources is patient specific, this process insures that the maximum benefit of standardization/optimization is achieved.

Again, as was described initially, while the application of the present invention is described in the context of the medical field, the present invention is also applicable to other fields in which a procedure is performed. Wherever a bill of resources is used in order to schedule, order, inventory, allocate, or otherwise assist in assurance that certain resources are available during the performance of a procedure, this technique is applicable. Furthermore, this method may be integrated into the business operations of an organization which is performing procedures to link with cost recovery, accounting, personnel, physical plant management, etc. systems in order to allow for the sharing of information in the entire business operation. For example, in the medical environment, the present invention may be used with supply utilization/management systems in order to provide procedure cost information to the billing department of a hospital for the billing of a patient. Similarly, the present invention can be used in connection with the accounting systems of a business in order to insure that the most effective use of supplies is being made and to help identify strategies for cost reduction.

The above-described embodiments are capable of numerous substitutions, deletions, modification and changes without departing from the scope of the claims set forth below. For example, the present invention could be implemented in a variety of manners, including various computer platforms, operating systems, programming languages, etc., without departing from the scope of the claims. In fact, although specific information concerning the software implementation of the present invention is given herein, one skilled in the art, with this description, could easily adapt the present invention to implementation on almost any computer platform/operating system/database software/programming language combination presently on the market, all of which may be done without departing from the scope of the claims.

What is claimed is:

1. An information management system for producing at least one standard bill of resources based on a plurality of bills of resources, where each of the plurality of bills of resources each include a list of resources to be utilized in performing a procedure, the system comprising:

a general purpose computer system, including:
  storage means for storing information related to the plurality of bills of resources;
  processing means for processing instructions related to producing the at least one standard bill of resources;
  display means for presenting the at least one standard bill of resources in a human perceptible format; and
  input means for receiving user input related to producing the at least one standard bill of resources;

information management software executed by the general purpose computer system, including:
  node software objects, each providing a health-care information management function, including:
    a clinical pathway node software object for selectively creating, managing, and maintaining user-defined, user-configurable clinical pathway module software objects adapted to function with the clinical pathway node software object and representing provider-specific procedural templates of the information related to the bills of resources, the clinical pathway module software objects including:

resource software objects, corresponding to resources to be used in providing health care services, the resources listed in the plurality of bills of resources; and container software objects for containing software objects having at least one common characteristic;

a case management node software object for selectively creating, managing, and maintaining a user-defined, user-configurable case management module software object adapted to function with the case management node software object from the clinical pathway module software object, the case management module software object representing a selected clinical pathway module software object as modified to reflect a prospective patient-specific case, and containing patient-specific information, and adapted to receive additional patient specific information; and a bill of resources standardization review node software object for selectively creating, managing, and maintaining at least one user-defined, user-configurable model module software object adapted to function with the bill of resources standardization review node software object and the case management module software object, the model module software object representing the case management module software object as modified by at least the patient-specific information to reflect a historical patient-specific case by:

selecting selected bills of resources from the plurality of bills of resources;

developing models corresponding to the selected bills of resources, the models including values which correspond to a number of units of given resources from the selected bills of resources;

manipulating the models mathematically to highlight similarities and dissimilarities of defined characteristics in the models;

expressing the manipulated models in a format in which a relative position of each of the manipulated models may be determined, the relative position of each of the manipulated models reflecting the degree of similarity or dissimilarity to the other manipulated models;

analyzing the selected bills of resources based upon the expression of the manipulated models; and producing the at least one standard bill of resources based on the analysis of the selected bills of resources.

2. The system of claim 1 wherein the bill of resources standardization review node software object manipulates the models mathematically by:

selecting a number of dimensions in which each manipulated model will be expressed; and manipulating each model in accordance with a mathematical algorithm such that each manipulated model is expressible in the desired number of dimensions.

3. The system of claim 1 wherein the bill of resources standardization review node software object manipulates the models mathematically by:

arranging the manipulated models in a matrix in which each manipulated model occupies a column of the matrix and each different resource occupies a row of the matrix, the number of columns equal to the number of models and the number of rows equal to the total number of different resources present in the bills of resources which are represented by the manipulated models;

selecting a desired dimension for expression of the models; and performing a matrix manipulation on the matrix according to a mathematical algorithm to reduce the number of rows of the matrix to the selected desired dimension for expression, where the mathematical algorithm is selected to highlight similarities or dissimilarities among the models.

4. The system of claim 3 wherein the matrix manipulation comprises matrix factorization and rank reduction.

5. The system of claim 4 wherein the matrix factorization technique is singular value decomposition.

6. The system of claim 1 wherein the bill of resources standardization review node software object selects the selected bills of resources from a group of resources representing the same procedure performed by different persons, and analyzes the selected bills of resources by identifying similarities and dissimilarities of resource utilization among the different persons performing the procedures.

7. The system of claim 6 wherein the bill of resources standardization review node software object produces the at least one standard bill of resources by developing a number of standard bills of resources for the procedure analyzed such that each of the different persons performing the procedure is using one of the standard bills of resources in performing the procedure, the number of standard bills of resources being less than the original number of bills of resources analyzed.

8. The system of claim 1 wherein the bills of resources to be analyzed reflect multiple performances of a given procedure by the same person, where differences in the bills of resources reflect different resource utilization among the performances of the procedure, and the bill of resources standardization review node software object analyzes the selected bills of resources by consideration of the deviation in resource utilization among the performances of the procedure.

9. The system of claim 8 wherein the bill of resources standardization review node software object analyzes the selected bills of resources by identifying inefficient deviations among the multiple performances of the given procedure by the same person, and produces the at least one standard bill of resources by developing the at least one standard bill of resources to minimize such deviations in future performances of the procedure by the person.

10. The system of claim 1 wherein the selected bills of resources include bills of resources from more than one procedure, and wherein the bill of resources standardization review node software object analyzes the expressed models by identifying standardization opportunities across different procedures.

11. The system of claim 1 wherein the selected bills of resources include partial bills of resources which are limited to only certain types or categories of resources in order to identify standardization opportunities among limited types or categories of resources common to the bills of resources.

12. The system of claim 8 wherein the bill of resources standardization review node software object develops the models of the selected bills of resources by filtering the selected bills of resources such that only certain resources from the bills of resources are included in the models.

13. The system of claim 12 wherein the bill of resources standardization review node software object filters the selected bills of resources by the selective retention or exclusion of certain resources or categories of resources.

14. The system of claim 1 wherein the container software objects comprise a plurality of container software object types, each type providing a specific container software object functionality.

15. The system of claim 1 wherein the container software objects comprise:

a user-configurable care event container software object representing a specific health care services care event, the care event container software object functional to contain container software objects and resource software objects related to the specific health care services care event represented by the care event container software object; and a user-configurable bundle container software object functional to contain resource software objects corresponding to specific related health care resources which would be provided in a group or bundle.

16. The system of claim 1 further comprising data software objects selectively associated with a software object selected from the group consisting of the clinical pathway module software object, the case management module software object, and the container software object, the data software objects suitable for collecting and maintaining information related to the software object with which the data software object is selectively associated.

17. The system of claim 1 further comprising a library node software object for selectively creating, collecting, and organizing reusable, user-defined, user-configurable container software objects and resource software objects for use in the clinical pathway node software object and the case management node software object.

18. An information management system for producing at least one standard bill of resources based on a plurality of bills of resources, where each of the plurality of bills of resources each include a list of resources to be utilized in performing a procedure, the system comprising:

a general purpose computer system, including:
  storage means for storing information related to the plurality of bills of resources;
  processing means for processing instructions related to producing the at least one standard bill of resources;
  display means for presenting the at least one standard bill of resources in a human perceptible format; and
  input means for receiving user input related to producing the at least one standard bill of resources;

information management software executed by the general purpose computer system, including:
  node software objects, each providing a health-care information management function, including:
    a clinical pathway node software object for selectively creating, managing, and maintaining user-defined, user-configurable clinical pathway module software objects adapted to function with the clinical pathway node software object and representing provider-specific procedural templates of the information related to the bills of resources, the clinical pathway module software objects including:
      resource software objects, corresponding to resources to be used in providing health care services, the resources listed in the plurality of bills of resources; and
      container software objects for containing software objects having at least one common characteristic, wherein the container software objects comprise a plurality of container software object types, each type providing a specific container software object functionality, the container software objects including:
        a user-configurable care event container software object representing a specific health care services care event, the care event container software object functional to contain container software objects and resource software objects related to the specific health care services care event represented by the care event container software object; and
        a user-configurable bundle container software object functional to contain resource software objects corresponding to specific related health care resources which would be provided in a group or bundle;
  a case management node software object for selectively creating, managing, and maintaining a user-defined, user-configurable case management module software object adapted to function with the case management node software object from the clinical pathway module software object, the case management module software object representing a selected clinical pathway module software object as modified to reflect a prospective patient-specific case, and containing patient-specific information, and adapted to receive additional patient specific information;
  data software objects selectively associated with a software object selected from the group consisting of the clinical pathway module software object, the case management module software object, and the container software object, the data software objects suitable for collecting and maintaining information related to the software object with which the data software object is selectively associated; and
  a bill of resources standardization review node software object for selectively creating, managing, and maintaining at least one user-defined, user-configurable model module software object adapted to function with the bill of resources standardization review node software object and the case management module software object, the model module software object representing the case management module software object as modified by at least the patient-specific information to reflect a historical patient-specific case by:
    selecting selected bills of resources from the plurality of bills of resources;
    developing models corresponding to the selected bills of resources, the models including values which correspond to a number of units of given resources from the selected bills of resources;
    manipulating the models mathematically to highlight similarities and dissimilarities of defined characteristics in the models;
    expressing the manipulated models in a format in which a relative position of each of the manipulated models may be determined, the relative position of each of the manipulated models reflecting the degree of similarity or dissimilarity to the other manipulated models;
    analyzing the selected bills of resources based upon the expression of the manipulated models; and
    producing the at least one standard bill of resources based on the analysis of the selected bills of resources; and
  a library node software object for selectively creating, collecting, and organizing reusable, user-defined, user-configurable container software objects and resource software objects for use in the clinical pathway node software object and the case management node software object.

* * * * *